United States Patent
Lagree et al.

(10) Patent No.: US 11,446,541 B2
(45) Date of Patent: *Sep. 20, 2022

(54) EXERCISE MACHINE MONITORING AND INSTRUCTION SYSTEM

(71) Applicant: Lagree Technologies, Inc., Chatsworth, CA (US)

(72) Inventors: Sebastien Anthony Louis Lagree, Chatsworth, CA (US); Andy H. Gibbs, Tucson, AZ (US); Samuel D. Cox, Yuba, CA (US); Todd G. Remund, Yuba, CA (US)

(73) Assignee: Lagree Technologies, Inc., Chatsworth, CA (US)

(*) Notice: Subject to any disclaimer, the term of this patent is extended or adjusted under 35 U.S.C. 154(b) by 174 days.

This patent is subject to a terminal disclaimer.

(21) Appl. No.: 17/124,855

(22) Filed: Dec. 17, 2020

(65) Prior Publication Data
US 2021/0101048 A1   Apr. 8, 2021

Related U.S. Application Data

(63) Continuation of application No. 16/396,853, filed on Apr. 29, 2019, now Pat. No. 10,870,034, which is a
(Continued)

(51) Int. Cl.
*A63B 22/00* (2006.01)
*A63B 71/06* (2006.01)
(Continued)

(52) U.S. Cl.
CPC ........ *A63B 22/0087* (2013.01); *A63B 21/023* (2013.01); *A63B 22/0076* (2013.01);
(Continued)

(58) Field of Classification Search
CPC .............. A63B 22/0087; A63B 21/023; A63B 22/0076; A63B 71/0622; A63B 21/00065;
(Continued)

(56) References Cited

U.S. PATENT DOCUMENTS

| 1,621,477 A | 8/1925 | Pilates |
| 2,894,755 A | 7/1959 | Scelzo, Jr. |

(Continued)

FOREIGN PATENT DOCUMENTS

WO    2004096376    11/2004

OTHER PUBLICATIONS

Picture of Proformer Exercise Machine Developed by the Inventor, Sebastien Lagree; Dec. 31, 2008.
(Continued)

*Primary Examiner* — Garrett K Atkinson
(74) *Attorney, Agent, or Firm* — Neustel Law Offices

(57) ABSTRACT

An exercise machine monitoring and instruction system for the movement of an element of an exercise machine by an exerciser and providing automated feedback to the exerciser to help improve the exercise in real-time. The exercise machine monitoring and instruction system generally includes an exercise machine having a movable element that moves between a first position and a second position in a reciprocating manner, a sensor that detects a real-time position of the movable element, a processor in communication with the sensor to receive the real-time position data from the sensor related to a position of the movable element and a feedback device in communication with the processor that provides real-time instructions to the exerciser on how to adjust their workout to achieve a desired result.

46 Claims, 13 Drawing Sheets

Related U.S. Application Data continuation of application No. 16/105,163, filed on Aug. 20, 2018, now Pat. No. 10,272,285, which is a continuation of application No. 15/072,840, filed on Mar. 17, 2016, now Pat. No. 10,052,518.

(60) Provisional application No. 62/134,373, filed on Mar. 17, 2015.

(51) Int. Cl.
*A63B 21/02* (2006.01)
*G09B 19/00* (2006.01)
*G16H 40/63* (2018.01)
*G06Q 10/06* (2012.01)
*G16H 20/30* (2018.01)
*A63B 21/00* (2006.01)
*A63B 21/22* (2006.01)
*A63B 71/00* (2006.01)
*A63B 21/04* (2006.01)
*A63B 24/00* (2006.01)

(52) U.S. Cl.
CPC ..... *A63B 71/0622* (2013.01); *G06Q 10/0639* (2013.01); *G09B 19/0038* (2013.01); *G16H 20/30* (2018.01); *G16H 40/63* (2018.01); *A63B 21/00065* (2013.01); *A63B 21/0428* (2013.01); *A63B 21/153* (2013.01); *A63B 21/225* (2013.01); *A63B 2022/0079* (2013.01); *A63B 2024/0081* (2013.01); *A63B 2071/0081* (2013.01); *A63B 2071/063* (2013.01); *A63B 2071/0655* (2013.01); *A63B 2208/0204* (2013.01); *A63B 2208/0233* (2013.01); *A63B 2220/20* (2013.01); *A63B 2220/30* (2013.01); *A63B 2225/09* (2013.01); *A63B 2225/107* (2013.01); *A63B 2225/20* (2013.01); *A63B 2225/50* (2013.01); *A63B 2230/75* (2013.01)

(58) Field of Classification Search
CPC . A63B 21/0428; A63B 21/153; A63B 21/225; A63B 2022/0079; A63B 2024/0081; A63B 2071/0081; A63B 2071/063; A63B 2071/0655; A63B 2208/0204; A63B 2208/0233; A63B 2220/20; A63B 2220/30; A63B 2225/09; A63B 2225/107; A63B 2225/20; A63B 2225/50; A63B 2230/75; G06Q 10/0639; G09B 19/0038; G16H 20/30; G16H 40/63
See application file for complete search history.

(56) References Cited

U.S. PATENT DOCUMENTS

| | | | |
|---|---|---|---|
| 3,730,531 A | 5/1973 | Zega | |
| 3,770,267 A | 11/1973 | McCarthy | |
| 4,437,669 A | 3/1984 | Pelz | |
| 4,506,884 A | 3/1985 | Hankin | |
| 4,759,540 A | 7/1988 | Yu | |
| 4,798,378 A | 1/1989 | Jones | |
| 5,066,005 A | 11/1991 | Luecke | |
| 5,263,913 A | 11/1993 | Boren | |
| 5,429,565 A | 7/1995 | Hagg | |
| D362,700 S | 9/1995 | Breibart | |
| 5,527,041 A | 6/1996 | Terry, III | |
| 5,584,783 A | 12/1996 | Hagg | |
| 5,586,941 A | 12/1996 | Klearman | |
| D382,319 S | 8/1997 | Gerschefske | |
| 5,681,249 A | 10/1997 | Endelman | |
| 5,885,197 A | 3/1999 | Barton | |
| 5,967,955 A | 10/1999 | Westfall | |
| 6,152,856 A * | 11/2000 | Studor | A63F 13/65 482/4 |
| 6,179,753 B1 | 1/2001 | Barker | |
| 7,163,500 B2 | 1/2007 | Endelman | |
| 7,192,387 B2 * | 3/2007 | Mendel | A63B 24/00 482/8 |
| 7,803,095 B1 | 9/2010 | Lagree | |
| 7,914,420 B2 * | 3/2011 | Daly | A63B 24/00 482/901 |
| 7,931,570 B2 | 4/2011 | Hoffman | |
| 8,021,242 B1 | 9/2011 | Tennison | |
| 8,641,585 B2 | 2/2014 | Lagree | |
| 8,740,758 B2 | 6/2014 | Sandvig | |
| 8,911,328 B2 * | 12/2014 | Alessandri | G16H 20/30 482/901 |
| 9,011,293 B2 * | 4/2015 | Shavit | G09B 19/0038 482/8 |
| 9,089,759 B1 | 7/2015 | Moschillo | |
| 9,227,124 B1 | 1/2016 | Sparks | |
| 9,480,876 B1 | 11/2016 | Blacklock | |
| 9,808,662 B1 | 11/2017 | File | |
| 10,046,193 B1 | 8/2018 | Aronson | |
| 10,220,244 B2 | 3/2019 | Lagree | |
| 2001/0056011 A1 | 12/2001 | Endelman | |
| 2003/0119635 A1 | 6/2003 | Arbuckle | |
| 2005/0130810 A1 | 6/2005 | Sands | |
| 2005/0164856 A1 | 7/2005 | Parmater | |
| 2006/0046914 A1 | 3/2006 | Endelman | |
| 2006/0199712 A1 | 9/2006 | Barnard | |
| 2006/0223681 A1 | 10/2006 | Loane | |
| 2008/0070765 A1 | 3/2008 | Brown | |
| 2008/0248935 A1 | 10/2008 | Solow | |
| 2010/0227748 A1 | 9/2010 | Campanaro | |
| 2011/0143898 A1 | 6/2011 | Trees | |
| 2011/0166002 A1 | 7/2011 | Savsek | |
| 2011/0172069 A1 | 7/2011 | Gerschefske | |
| 2011/0275447 A1 | 11/2011 | Jasinski | |
| 2012/0088641 A1 | 4/2012 | Shah | |
| 2012/0190505 A1 * | 7/2012 | Shavit | A63B 24/0062 482/8 |
| 2012/0283078 A1 | 11/2012 | Solow | |
| 2012/0295722 A1 | 11/2012 | Vancho | |
| 2012/0295771 A1 | 11/2012 | Lagree | |
| 2013/0102406 A1 | 4/2013 | Yu | |
| 2013/0116807 A1 * | 5/2013 | Cheung | G06F 17/40 700/91 |
| 2013/0196835 A1 | 8/2013 | Solow | |
| 2014/0005007 A1 | 1/2014 | Ho | |
| 2014/0011645 A1 | 1/2014 | Johnson | |
| 2014/0024508 A1 | 1/2014 | Hinds | |
| 2014/0100089 A1 | 4/2014 | Kermath | |
| 2014/0121076 A1 | 5/2014 | Lagree | |
| 2014/0121078 A1 | 5/2014 | Lagree | |
| 2014/0121079 A1 | 5/2014 | Lagree | |
| 2014/0141948 A1 | 5/2014 | Aronson | |
| 2014/0155187 A1 | 6/2014 | Spelman | |
| 2014/0174174 A1 * | 6/2014 | Uehara | A61B 5/227 700/91 |
| 2015/0024914 A1 | 1/2015 | Lagree | |
| 2015/0057127 A1 | 2/2015 | Lagree | |
| 2015/0065318 A1 | 3/2015 | Lagree | |
| 2015/0072841 A1 | 3/2015 | Lagree | |
| 2015/0093732 A1 | 4/2015 | Ross | |
| 2015/0111706 A1 | 4/2015 | Broadhurst | |
| 2015/0141204 A1 | 5/2015 | Lagree | |
| 2015/0217164 A1 | 8/2015 | Lagree | |
| 2015/0220523 A1 | 8/2015 | Lagree | |
| 2015/0246263 A1 | 9/2015 | Campanaro | |
| 2015/0297944 A1 | 10/2015 | Lagree | |
| 2015/0343250 A1 | 12/2015 | Lagree | |
| 2015/0360068 A1 | 12/2015 | Lagree | |
| 2015/0360083 A1 | 12/2015 | Lagree | |
| 2015/0360113 A1 | 12/2015 | Lagree | |
| 2015/0364058 A1 | 12/2015 | Lagree | |
| 2015/0367162 A1 | 12/2015 | Mueller | |
| 2015/0367166 A1 | 12/2015 | Lagree | |
| 2016/0008657 A1 | 1/2016 | Lagree | |
| 2016/0059060 A1 | 3/2016 | Lagree | |

(56) References Cited

U.S. PATENT DOCUMENTS

| | | |
|---|---|---|
| 2016/0059061 A1 | 3/2016 | Lagree |
| 2016/0109218 A1 | 4/2016 | Austin |
| 2016/0271452 A1* | 9/2016 | Lagree .................. G16H 20/30 |
| 2017/0043210 A9 | 2/2017 | Lagree |
| 2017/0151459 A1 | 6/2017 | Abramovich |
| 2018/0008877 A1 | 1/2018 | Haycock |

OTHER PUBLICATIONS

Drawing of Proformer Exercise Machine Developed by the Inventor, Sebastien Lagree; 2008.

Picture of Proformer Redline Developed by the Inventor, Sebastien Lagree; 2008.

https://www.yelp.com/biz_photos/solidcore-washington-5?select=ywYl22p-_3f6JAJl5cXDWg; Picture of Solidcore Modification posted on Yelp website on Dec. 23, 2014.

Picture of Solidcore Machine believed to be from Solidcore's Facebook Webpage; Mar. 4, 2016.

hhttps://www.facebook.com/solidcorestudio/photos/a.147049612160841/478381339027665/?type=3&theater; Picture of Solidcore Machine from Facebook Webpage; Mar. 25, 2016.

https://www.facebook.com/solidcorestudio/photos/a.147049612160841/480088418856957/?type=3&theater; Picture of Solidcore Machine from Facebook Webpage; Mar. 28, 2016.

PCT Search Report Received from the International Searching Authority for PCT/US2016/022888.

PCT Preliminary Report on Patentability from International Searching Authority for PCT/US2016/022888.

* cited by examiner

*FIG. 5A*

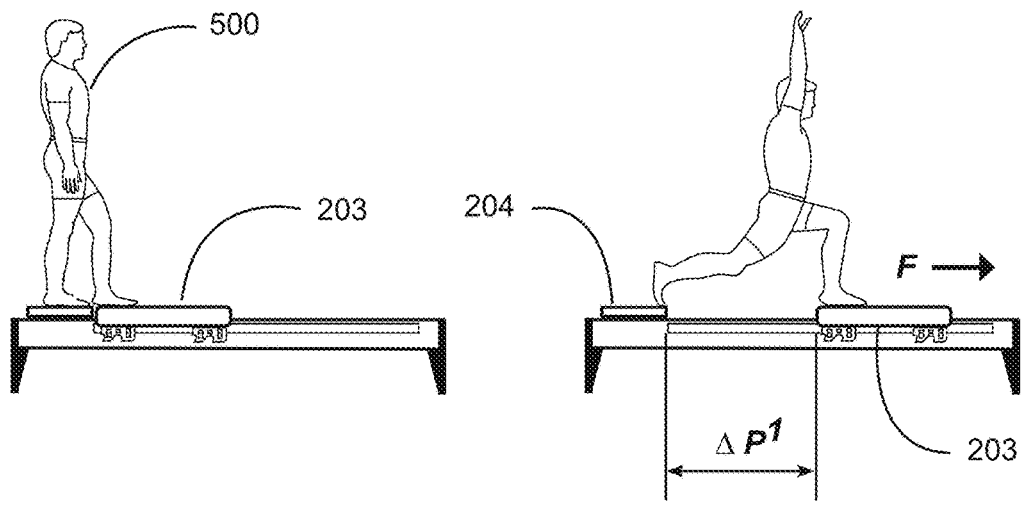

*FIG. 5B*

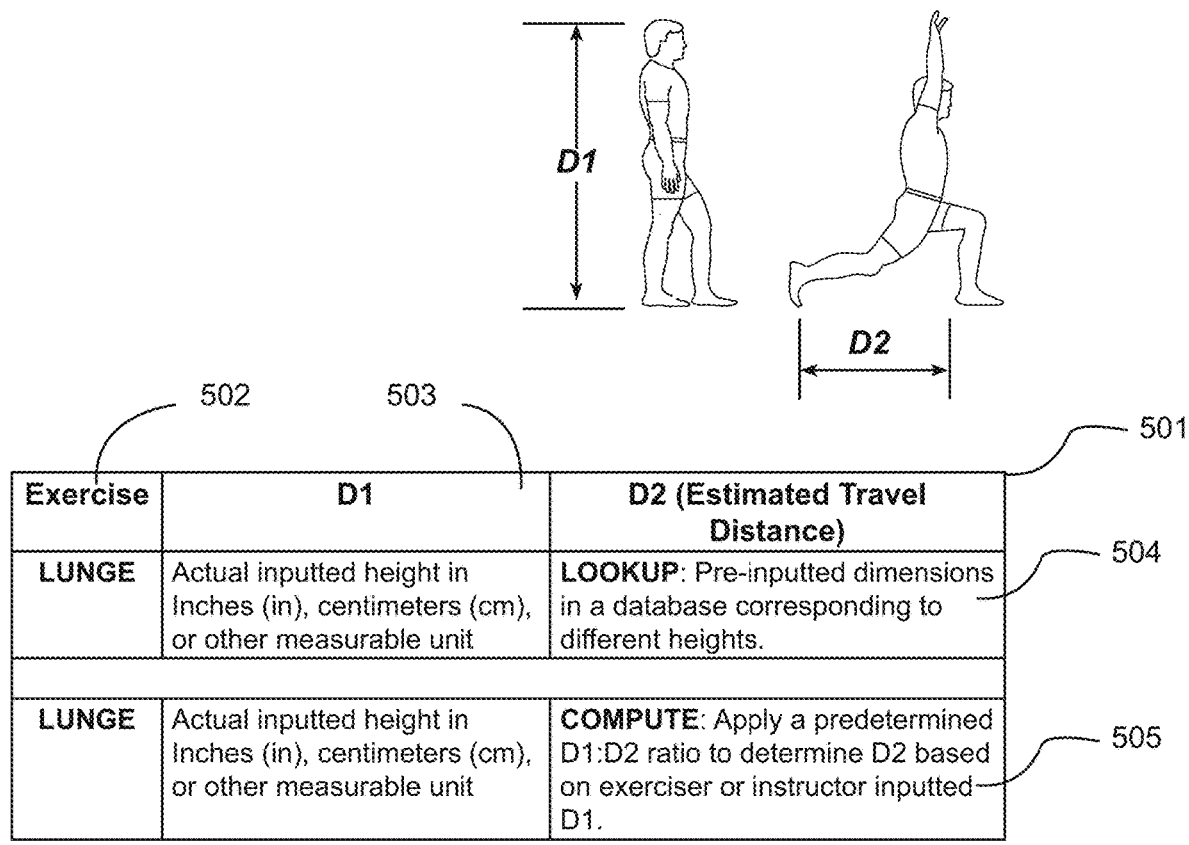

| Exercise | D1 | D2 (Estimated Travel Distance) |
|---|---|---|
| LUNGE | Actual inputted height in Inches (in), centimeters (cm), or other measurable unit | LOOKUP: Pre-inputted dimensions in a database corresponding to different heights. |
| LUNGE | Actual inputted height in Inches (in), centimeters (cm), or other measurable unit | COMPUTE: Apply a predetermined D1:D2 ratio to determine D2 based on exerciser or instructor inputted D1. |

FIG. 7

RANGE-OF-MOTION

| Virtual Instructor Real-Time Analysis And Feedback ||||
| Exercise | Range Of Motion (In) | | Deviation | FEEDBACK |
| | Actual | Ideal | Actual-Ideal | |
| Lunge | 26 | 31 | -5 | Fitness Impact: EXERCISER IS NOT REALIZING COMPLETE WORKOUT BENEFITS.<br><br>Instruction: Extend the front foot farther forward (push the carriage farther during each repetition.<br><br>Methot of Feedback:<br>Visual: Lights blink at a different rate, and stop blinking when reaching carriage position for ideal range of motion<br><br>Visual: Lights change color when approaching and/or reaching carriage position for ideal range of motion<br><br>Audible: Tone change in audible buzzer when reaching carriage position for ideal range of motion.<br><br>Audible: Prerecorded voice instructing exerciser to extend the front foot farther forward, changing to voice instruction to stop the motion and return to the starting position after reaching the carriage position for ideal range of motion.<br><br>Tactile: Vibration frequency of one or more exercise platforms changes upon approaching and/or reaching carriage position for ideal range of motion. |
| Lunge | 33 | 31 | +2 | Fitness Impact: EXERCISER IS OVER-EXTENDING. INJURY POSSIBLE.<br><br>Instruction: Reduce extension.<br><br>Methot of Feedback:<br>Visual: Lights blink to warn of over-extension after passing ideal carriage position.<br><br>Visual: Lights change to a warning color after passing the ideal carriage position.<br><br>Audible: Emergency tone when exceeding ideal carriage position.<br><br>Audible: Prerecorded voice warning after exceeding ideal carriage position.<br><br>Tactile: Noted change in vibration of exercise platform after exceeding ideal carriage position. |

*FIG. 8*

REPETITION SPEED

| Virtual Instructor Real-Time Analysis And Feedback ||||
|---|---|---|---|
| Exercise | Repetition Speed (sec) || Deviation | FEEDBACK |
| | Actual | Ideal | | |
| Lunge | 4.60 | 4.0 | +0.6 | Fitness Impact: GOING TOO SLOW RESULTS IN REDUCED NUMBER OF REPETITIONS BEFORE MOVING TO THE NEXT TIMED EXERCISE SEQUENCE. LENGTHENS DURATION OF WORKOUT SESSION.<br><br>Instruction: Perform repetitions faster. Speed up.<br><br>Methot of Feedback:<br>Visual: Lights blink at a fast rate ti indicate "speed up".<br><br>Visual: Lights change to a color indicating "go faster".<br><br>Audible: Tone changes to a frequency indicating "speed up".<br><br>Audible: Prerecorded voice instructing exerciser to complete each repetition faster.<br><br>Tactile: Vibration frequency changes to indicate "speed up". |
| Lunge | 3.15 | 4.0 | -0.85 | Fitness Impact: GOING TOO FAST. NOT RECEIVING COMPLETE WORKOUT BENEFIT.<br><br>Instruction: Reduce extension.<br><br>Methot of Feedback:<br><br>Visual: Lights blink at a slow rate ti indicate "slow down".<br><br>Visual: Lights change to a color indicating "caution; slow down".<br><br>Audible: Tone changes to a frequency indicating "slow down".<br><br>Audible: Prerecorded voice instructing exerciser to complete each repetition slower.<br><br>Tactile: Vibration frequency changes to indicate "slow down". |

FIG. 9

EXERCISE SESSION: 30 MINUTES

Current Exercise: LUNGE
Repetition Count Down: 5

| Machine No. | Class Rank | Your Exercise Time | Rage of Motion Accuracy | Repetition Accuracy | Efficiency / Smoothness | Calories | Struggle Warning |
|---|---|---|---|---|---|---|---|
| 11 | 1 | 17:37 | 100% | 100% | 99% | 184 | |
| 12 | 2 | 17:37 | 98% | 94% | 97% | 172 | |
| 3 | 3 | 17:37 | 100% | 93% | 97% | 200 | |
| 7 | 4 | 17:37 | 95% | 100% | 86% | 145 | |
| 4 | 4 | 17:37 | 90% | 99% | 86% | 205 | |
| 10 | 4 | 17:37 | 93% | 97% | 86% | 173 | |
| 2 | 5 | 17:37 | 89% | 99% | 85% | 168 | |
| 6 | 6 | 17:37 | 85% | 98% | 83% | 188 | |
| 8 | 7 | 17:37 | 85% | 100% | 80% | 157 | |
| 1 | 8 | 17:37 | 82% | 93% | 79% | 144 | |
| 5 | 8 | 17:30 | 75% | 90% | 71% | 151 | #### |
| 9 | 9 | 17:21 | 45% | 91% | 62% | 120 | #### |

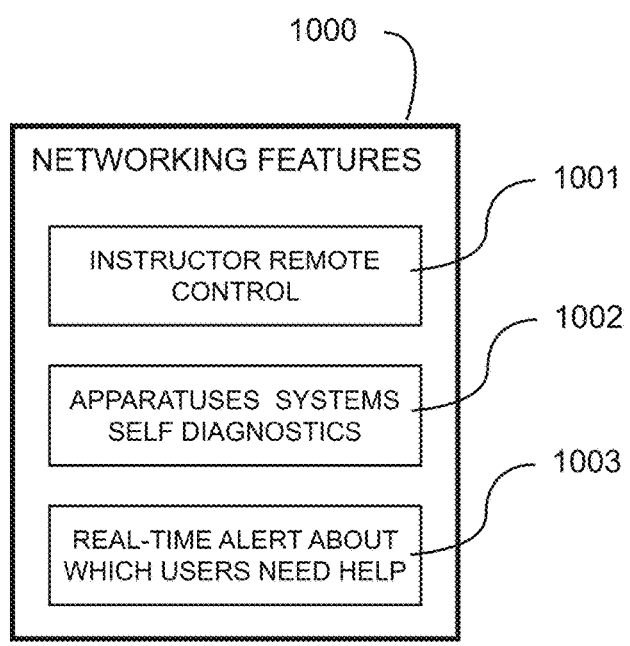

FIG. 10

NETWORKING FEATURES

- INSTRUCTOR REMOTE CONTROL
- APPARATUSES SYSTEMS SELF DIAGNOSTICS
- REAL-TIME ALERT ABOUT WHICH USERS NEED HELP

FIG. 11

| Machine No. | Class Rank | Exercise Time | Rage of Motion Accuracy | Repetition Accuracy | Efficiency | Calories | Struggle Warning |
|---|---|---|---|---|---|---|---|
| 9 | 9 | 28:18 | 45% | 91% | 62% | 258 | #### |

POST WORKOUT DIAGNOSTICS

Great effort, but it appears that you were struggling throughout this session. One possible cause may be that you were working against too much spring resistance, which can cause injuries.

Your total rest time was 1 minute, 42 seconds.

TO IMPROVE: Begin by SIGNIFICANTLY REDUCING spring resistance at the start of your next session. This will allow you to complete the repetitions faster, and extend to your full range of motion.

FIG. 13

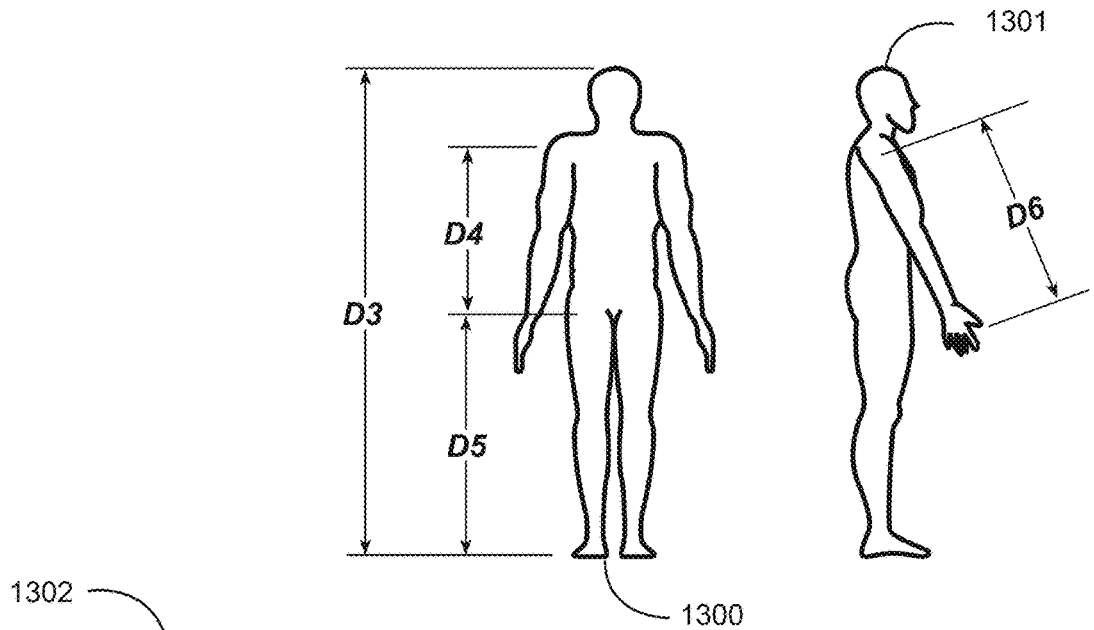

| ESTIMATING SEAT TRAVEL BASED ON PHYSIOLOGICAL MEASUREMENTS ||||| |
|---|---|---|---|---|
| D3 | D4 | D5 | D6 | Estimating Seat Travel |
| Actual inputted height in Inches (in), centimeters (cm), or other measurable unit | Actual inputted torso length, or inferred relative to heights based on a given percentile of the population | Actual inputted hip to heal length, or inferred relative to heights based on a given percentile of the population | Actual inputted arm length, or inferred relative to heights based on a given percentile of the population | LOOKUP: Pre-inputted dimensions in a database corresponding to different D3 and/or D3, D5. OR COMPUTE: Apply a predetermined D3:D5 ratio to correlate leg lentgh to seat travel. |

| ESTIMATING ROPE TRAVEL BASED ON PHYSIOLOGICAL MEASUREMENTS ||||| |
|---|---|---|---|---|
| D3 | D4 | D5 | D6 | Estimating Rope Travel |
| Actual inputted height in Inches (in), centimeters (cm), or other measurable unit | Actual inputted torso length, or inferred relative to heights based on a given percentile of the population | Actual inputted hip to heal length, or inferred relative to heights based on a given percentile of the population | Actual inputted arm length, or inferred relative to heights based on a given percentile of the population | LOOKUP: Pre-inputted dimensions in a database corresponding to different D3 and/or D3, D6. OR COMPUTE: Apply a predetermined D3:D5 ratio to correlate arm lentgh to rope travel. Apply a formula accounting for rope travel relative to leg length, plus adidtional rope travel as back is angled at $\theta$. OR Seat to rope travel ratio. |

EXERCISE MACHINE MONITORING AND INSTRUCTION SYSTEM

CROSS REFERENCE TO RELATED APPLICATIONS

The present application is a continuation of U.S. application Ser. No. 16/396,853 filed on Apr. 29, 2019 which issues as U.S. Pat. No. 10,870,034 on Dec. 22, 2020, which is a continuation of U.S. application Ser. No. 16/105,163 filed on Aug. 20, 2018 now issued as U.S. Pat. No. 10,272,285, which is a continuation of U.S. application Ser. No. 15/072,840 filed on Mar. 17, 2016 now issued as U.S. Pat. No. 10,052,518, which claims priority to U.S. Provisional Application No. 62/134,373 filed Mar. 17, 2015. Each of the aforementioned patent applications, and any applications related thereto, is herein incorporated by reference in their entirety.

STATEMENT REGARDING FEDERALLY SPONSORED RESEARCH OR DEVELOPMENT

Not applicable to this application.

BACKGROUND

Field

Example embodiments in general relate to an exercise machine monitoring and instruction system for monitoring the movement of an element of an exercise machine by an exerciser and providing automated feedback to the exerciser to help improve the exercise in real-time.

Related Art

Any discussion of the related art throughout the specification should in no way be considered as an admission that such related art is widely known or forms part of common general knowledge in the field.

Conventional Pilates apparatuses are well known worldwide throughout the fitness industry, and are generally comprised of a rectangular, horizontal base structure with parallel rails aligned with the major longitudinal axis of the rectangular structure. A sliding carriage is positioned upon the parallel rails and is attached to a first end of the structure by one or more spring biasing means that produce an exercise resistance. Sliding the carriage away from the first end of the apparatus creates a workload against which exercises can be safely and beneficially performed. The slidable carriage may freely slide along the parallel rails substantially the entire longitudinal length of the apparatus between the first and second ends of the apparatus.

The method by which an exerciser executes an exercise upon a Pilates apparatus is not arbitrary. Each and every exercise comprises at least these four components, although some exercises may encompass other performance variables:

a) A first time element (duration of the total exercise session, for instance, 45 minutes);

b) A second time element (the duration of one repetition of any given exercise, a repetition being defined as the routine that slides the carriage away from a starting position to a distal position upon the rails, and subsequently returning the carriage back to the starting point);

c) A distance element (the distance that an exerciser should move the carriage distal to the starting point before pausing, and immediately thereafter returning the carriage to the starting position).

d) Workload (each exerciser will be required to attach one or more tension devices (e.g. resistance springs) between the slidable carriage and the stationary first end of the apparatus, thereby creating an exercise resistance workload.

The proper distance that the carriage should be moved away from its starting position during an exercise is substantially determined by the human range of motion of the exerciser. Taller exercisers will invariably move the carriage a further distance from the starting point than a shorter exerciser, merely as a function of the relatively different limb lengths. Coaching of Pilates exercisers is required to ensure that each exercise is performed within the certain time, range of motion distance and workload parameters established for each exerciser by the coach. A Pilates coach is most often referred to by those in the industry as an instructor.

The coaching process follows three fundamental steps, although some methods employ many more additional steps. The fundamental steps are:

a) Exerciser performs an exercise;

b) Instructor observes the performance, and collects empirical data related to form, speed, workload and other performance parameters;

c) Instructor analyses the performance data;

d) Instructor provides the exerciser with instructions to improve performance.

Typically, each exercise within a routine of exercises is performed only for a few minutes before moving to a new exercise. Each exercise is comprised of a given number of repetitions that should be completed within the given time.

Pilates instructors provide direction to an exerciser as a means to increase the safety and effectiveness of the workout, such direction including any of the following:

a) Increase or decrease carriage travel distance. This instruction is based on the height of the exerciser, and the exerciser's normal range of motion;

b) Increase or decrease the speed at which each repetition is being performed. The speed of performing each exercise repetition should be substantially the same for all exercisers in the class;

c) Increase or decrease workload. Resistance settings that are too high or too low result in decreased exercise benefits, and typically negatively impact the speed and carriage travel distance as just described.

As can be readily understood, an instructor instructing a class of a dozen or more Pilates exercisers is unable to provide one-on-one coaching for every exerciser, or for every repetition performed each exerciser throughout the class exercise period. Understanding these well-known problems and limitations with traditional Pilates apparatuses, an instructor traditionally moves about the class of Pilates exercisers to coach each exerciser individually, advising on the proper speed and carriage travel for each exerciser's unique range or motion. Since an instructor can reasonably spend only a small amount to time coaching only one exerciser at a time, many exercisers in a large Pilates exercise class will never receive thorough coaching on proper exercise movement before the class is required to change to a new exercise.

As just described, and despite the best efforts of Pilates class instructors, most Pilates exercisers are left to perform exercises substantially self-directed throughout exercise class periods, and without the benefit of persistent form, speed and workload monitoring, or corrective instruction from an instructor. The lack of continual performance monitoring results in a less efficient and less effective workout than would otherwise be achieved by exercisers who have the benefit of persistent coaching.

Therefore, one well-known problem is that traditional Pilates apparatuses fail to provide any means of measuring the travel distance of a slidable carriage during exercise. As a consequence of the inability to measure carriage travel distance, traditional Pilates apparatuses are not able to correlate carriage travel distances with the corresponding proper range of motion of exercisers of different heights.

Another well-known problem is that traditional Pilates apparatuses fail to provide any means to determine the velocity at which the slidable carriage moves during the performance of an exercise. As a consequence of the inability to measure carriage velocity during exercises, traditional Pilates apparatuses are not able to provide exercisers with corrective information to speed up or slow down their exercise repetition speed.

Another problem with traditional Pilates apparatuses is that they do not provide a means for exercisers of different heights to determine the proper velocity they should move the slidable carriage during work or recovery phases of an exercise repetition. The result is that many exercisers ultimately perform many repetitions of many exercises incorrectly, in some cases, exercisers moving the carriage too far and over extend their normal range of motion, thereby causing injury to joints or soft tissue, or in other cases moving the carriage too slowly or quickly, thereby missing the strength benefit of controlled-speed exercising.

Pilates instructors and others in the exercise industry will recognize the enormous benefit of a system and method that would simultaneously coach all of the exercisers throughout the duration of a Pilates class, providing exercisers with instruction on the proper range of motion and repetition speed for each exercise, and proper workload settings. Further, Pilates studio owners, managers and instructors will appreciate the commercial value of improved Pilates apparatuses that provide exercisers with safer, more efficient workouts that burn more calories within a specified Pilates class period, especially when compared to competitors relying on traditional apparatuses and one-on-one coaching.

SUMMARY

An example embodiment of the present invention is directed to an exercise machine monitoring and instruction system. The exercise machine monitoring and instruction system includes an exercise machine having a movable element that moves between a first position and a second position in a reciprocating manner, a sensor that detects a real-time position of the movable element, a processor in communication with the sensor to receive the real-time position data from the sensor related to a position of the movable element and a feedback device in communication with the processor that provides real-time instructions to the exerciser on how to adjust their workout to achieve a desired result.

Pilates exercises are designed by knowledgeable Pilates exercise instructors with the objectives of maximizing the workload on targeted muscles or muscle groups, and exercising the targeted muscles or muscle groups through a prescribed range of motion. Exercisers upon a Pilates apparatus are properly performing exercises when a plurality of previously established parameters are met. Coaching is a process that defines the exercise performance objectives, monitors the exerciser's actual performance against the objectives, and provides instructions back to the exerciser with regard to modifications to range of motion, speed and/or workload as required to perform more in line with the established performance objectives. More specifically, exerciser performance data observed by an instructor is empirical, but analysis of the data by an instructor is subjective, and limited to the one person being observed, and only for the period of time of observation.

The automated coaching system of the improved Pilates apparatus provides for the persistent monitoring, analysis and instruction of all exercisers in a Pilates class simultaneously, throughout the duration of a class session. Each apparatus therefore provides for exercise performance coaching by the following process:

A. Collection of Known Data: Continual, real time data collection of carriage travel distance, direction, speed, and unique exerciser anthropometric measurements (inputted exerciser height and/or body part measurement);

B. Computed Data Analytics: Computing actual carriage travel direction, velocity, and repetition cyclic rate;

C. Data Comparison: Comparing actual data of (B) to targeted carriage travel, velocity and cyclic rate established for the given exercise. The actual data is further analyzed based on the exerciser's physiology.

D. Instructional Feedback: Based on the data comparison (C), the present invention provides feedback to the exerciser, the feedback including, but not limited to recommended increases or decreases to the carriage speed, carriage travel distance, repetition cyclic rate, or workload resistance.

Further, the new and novel system and method of automated coaching of Pilates exercisers provides for real time computation of physiological performance data, such as caloric burn rate, or total calories consumed during the exercise class period.

Those skilled in the art will appreciate that the nearly 100 year body of work teaching the Pilates exercise method does not teach the unique and valuable automated coaching or performance monitoring functions just described.

A. Collection of Known Data

Therefore, one exemplary embodiment of the present invention is a new and novel system to measure travel distance, position and speed of a slidable carriage of a Pilates apparatus. Another exemplary embodiment of the present invention is a new and novel system providing for exercisers to input one or more dimensions relating to height or certain body parts as a means to determine appropriate range of motion during Pilates exercises.

B. Computed Data Analytics

Another exemplary embodiment of the present invention is a new and novel method of analyzing carriage speed, travel distance and travel direction to determine performance velocity of an exercise during the workload and recovery phases of each repetition of a Pilates exercise. Yet another exemplary embodiment of the present invention is a new and novel method of estimating the preferred travel distance of a slidable Pilates carriage based on the projected range of motion of exercisers of different heights. Another exemplary embodiment of the present invention is a new and novel method providing the for inputting of the resistance level against which an exercise is working, and further analyzing the workload relative to the speed and distance the workload is pushed by the exerciser as a means of determining energy output in calories during the course of an exercise session.

C. Data Comparison

Another exemplary embodiment of the present invention is a new and novel method of comparing an exerciser's actual performance data characteristics to a database of estimated performance characteristics accounting for (a) the relative height of the exerciser, and (b) the exercise being performed. Yet another exemplary embodiment of the present invention is a new and novel method of correlating the under or over performance of any exercise parameters by any exerciser with a corresponding instruction from a list of instructions, such instruction being meant to inform the exerciser of an appropriate action to correct any over or under performance practices.

D. Instructional Feedback

Another exemplary embodiment of the present invention is a visual instruction system of an improved exercise apparatus that informs an exerciser on the proper travel distance of a carriage on the first occurrence of the first repetition of a new exercise. Another exemplary embodiment of the present invention is a visual feedback system of an improved exercise apparatus that alerts an exerciser when they have achieved the proper physiological range of motion of the exercise. Yet another exemplary embodiment of the present invention is a visual feedback system of an improved exercise apparatus that alerts an exerciser when they have exceeded the proper physiological range of motion of the exercise. Another exemplary embodiment of the present invention is a visual feedback system of an improved exercise apparatus that alerts an exerciser when they have failed to achieve the proper physiological range of motion of the exercise. Yet exemplary embodiment of the present invention is a visual feedback system of an improved exercise apparatus that alerts an exerciser when they are performing each repetition of an exercise at a cyclic rate that exceeds the recommended cyclic rate at which the exercise is intended to be performed. Yet another exemplary embodiment of the present invention is a visual feedback system of an improved exercise apparatus that alerts an exerciser when they are performing each repetition of an exercise at a cyclic rate that is slower the recommended cyclic rate at which the exercise is intended to be performed. Still another exemplary embodiment of the present invention is a visual feedback system of an improved exercise apparatus that alerts an exerciser when they are performing each repetition of an exercise at a proper cyclic rate. Another exemplary embodiment of the present invention is a visual feedback system of an improved exercise apparatus that alerts an exerciser when the resistance setting of a Pilates apparatus should be changed to an increased or decreased resistance level. Another exemplary embodiment of the present invention is a visual feedback system of an improved exercise apparatus that alerts an exerciser when the exercise routine being performed on an exercise apparatus is about to end, or when the exercise is about to transition to a new and different exercise. Yet exemplary embodiment of the present invention is a visual feedback system of an improved exercise apparatus that informs an exerciser of the total time duration for which one or more exercises are to be performed. Still another exemplary embodiment of the present invention is a visual feedback system of an improved exercise apparatus that informs an exerciser of the exercising time remaining relative to the total time duration of the exercise or series of exercises. Another exemplary embodiment of the present invention is an audible or sensory feedback system that provides for instructional information to be communicated to an exerciser. Another exemplary embodiment of the present invention is an instructional system and method that uses one or more of visual, audible or sensory feedback as a means to communicate to the exerciser recommended corrections to speed, carriage travel distance, cyclic rate, or workload levels in order to more beneficially perform a Pilates exercise.

E. Exercise Performance Summary

Still another exemplary embodiment of the present invention is a system providing for informing an exerciser of the detailed performance of their exercise session, including but not limited to percent of time they were exercising within the targeted parameters, total exercise time, and total calories consumed during the exercise.

F. Variation for Rowing Machines and Other Exercise Machines

Still another exemplary embodiment of the present invention is a variation providing for analyzing form and efficiency of an exerciser upon an improved rowing machine apparatus. The exercise machine monitoring and instruction system may be used on various other types of exercise machines that have at least one element (e.g. carriage, handle, foot pedal, etc.) to be moved from a first position to a second position (preferably a reciprocating movement similar to or related to a Pilates machine or rowing machine).

There has thus been outlined, rather broadly, some of the features of the exercise machine monitoring and instruction system in order that the detailed description thereof may be better understood, and in order that the present contribution to the art may be better appreciated. There are additional features of the exercise machine monitoring and instruction system that will be described hereinafter and that will form the subject matter of the claims appended hereto. In this respect, before explaining at least one embodiment of the exercise machine monitoring and instruction system in detail, it is to be understood that the exercise machine monitoring and instruction system is not limited in its application to the details of construction or to the arrangements of the components set forth in the following description or illustrated in the drawings. The exercise machine monitoring and instruction system is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

Example embodiments will become more fully understood from the detailed description given herein below and the accompanying drawings, wherein like elements are represented by like reference characters, which are given by way of illustration only and thus are not limitative of the example embodiments herein.

FIG. 5A is an exemplary diagram showing a side view of a person exercising on a Pilates apparatus.

FIG. 5B is an exemplary diagram showing an illustration and chart to determine estimated range of motion.

FIG. 7 is an exemplary diagram showing real time analysis and feedback related to range of motion.

FIG. 8 is an exemplary diagram showing real time analysis and feedback related to exercise speed.

FIG. 9 is an exemplary diagram showing real time analysis of exercisers on a plurality of apparatuses within an exercise facility.

FIG. 10 is an exemplary diagram showing a block diagram of network features.

FIG. 11 is an exemplary diagram showing a representative post-exercise report of one exerciser.

FIG. 13 is an exemplary diagram showing anthropometric models and measurements correlating to range of motion.

DETAILED DESCRIPTION

Various aspects of specific embodiments are disclosed in the following description and related drawings. Alternate embodiments may be devised without departing from the spirit or the scope of the present disclosure. Additionally, well-known elements of exemplary embodiments will not be described in detail or will be omitted so as not to obscure relevant details. Further, to facilitate an understanding of the description, a discussion of several terms used herein follows.

The word "exemplary" is used herein to mean "serving as an example, instance, or illustration." Any embodiment described herein as "exemplary" is not necessarily to be construed as preferred or advantageous over other embodiments. Likewise, the term "embodiments" is not exhaustive and does not require that all embodiments include the discussed feature, advantage or mode of operation.

The word "instructor" as used herein means the knowledgeable person or persons guiding one or more exercisers in a Pilates class. Instructor shall also mean "coach" or "trainer" with no difference in meaning or intention. These descriptions are interchangeable.

The phrase "Pilates Method" as used herein means the body or aft related to the method of exercising on a Pilates apparatus. However, many adaptations of the Pilates Method are known. Therefore, Pilates Method shall also mean "Lagree Method" or any other non-specific method of exercising on a substantially horizontal exercise apparatus providing for a spring-biased slidable carriage. These descriptions are interchangeable.

Figure 1:
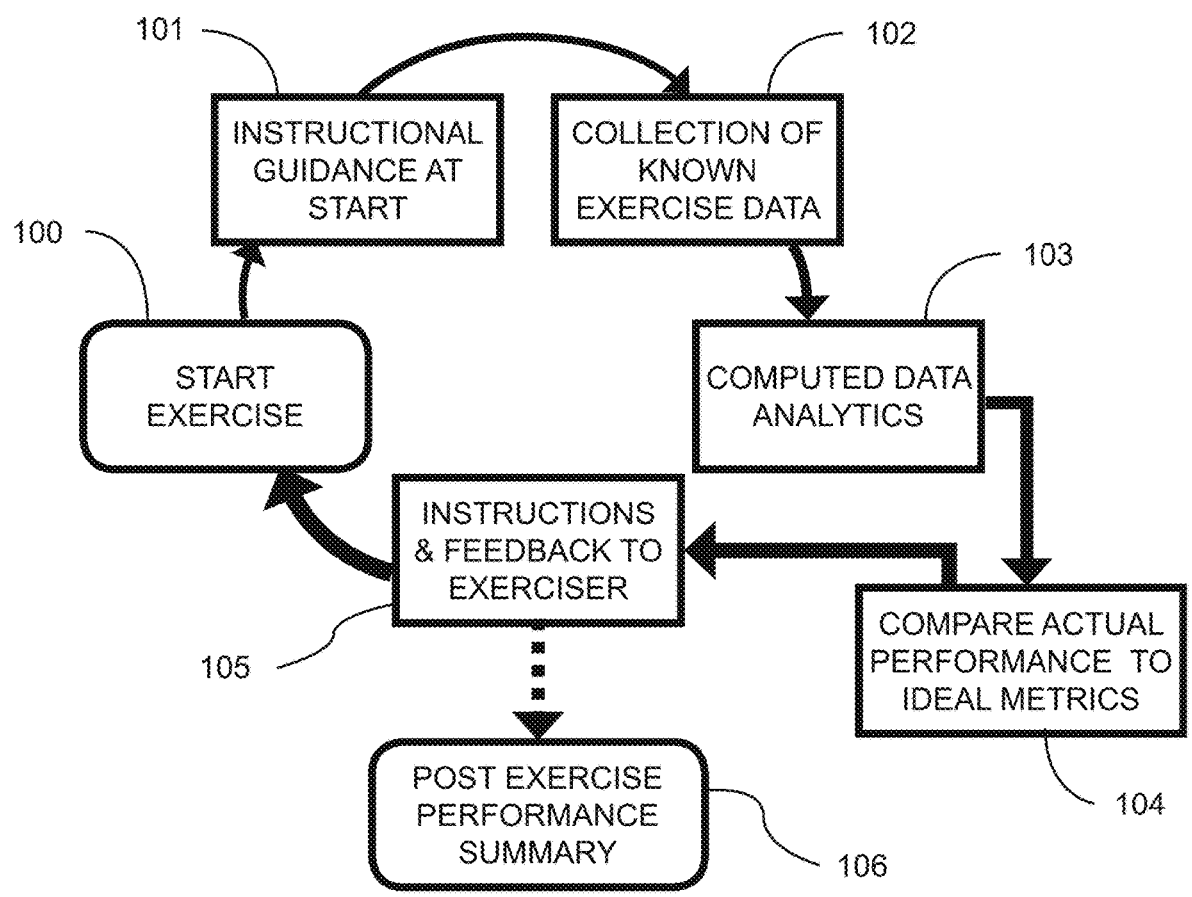
FIG. 1 is an exemplary diagram showing a flow chart of the virtual Pilates instructional process.

FIG. 1 is an exemplary diagram showing a flow chart of the virtual Pilates instructional process. As is well known in the fitness industry, exercisers performing an exercise for the first time require guidance. In the process shown in the drawing, an exerciser starts and exercise 100 on a Pilates apparatus, and is immediately directed on how far they should slide the slidable carriage on the first repetition of the exercise, the direction being made by one or more methods of instructional guidance 102 as will be fully described herein.

Upon completion of one first repetition of a first exercise, the system and method of the novel instructional process collects data 102 related to the carriage travel distance, travel direction, and travel speed, referred to herein as a portion of the "known data". The known data is subsequently analyzed 103 by means of a computer processor 10 (e.g. control unit, a computer, a mobile electronic device, etc.) in order process the known data into data format that may be compared to the estimated performance metrics expected of exercisers of similar height performing the same exercise on the same apparatus.

The actual performance data as analyzed 103 is then compared to the estimated ideal performance metrics 104 as a means to determine the accuracy and efficiency of the exerciser's performance against the estimated ideal performance. After analysis, as would be expected by analysis by a live person coaching the performance of an exerciser, instructions and feedback 105 are subsequently provided to the exerciser, the instructions thereby providing advice on corrections that should be made to the exerciser's performance of the exercise, for instance, advising the exerciser to increase or decrease the speed of each repetition of the exercise.

As the exerciser continues to exercise, the process is continually repeated, with the collection of known data being updated with each movement of the slidable carriage, and the refinements to corrective instructions being made and delivered back to the exerciser.

Upon completing the sequence of exercises performed during a Pilates workout session, the system and method of the present invention completes the analysis of the entire workout session, and delivers a post-exercise performance summary 106 to the exerciser for baseline performance reference, and as guidance as to corrective measures the exerciser should employ during their next workout session in order to improve their efficiency and fitness levels.

Figure 2A:
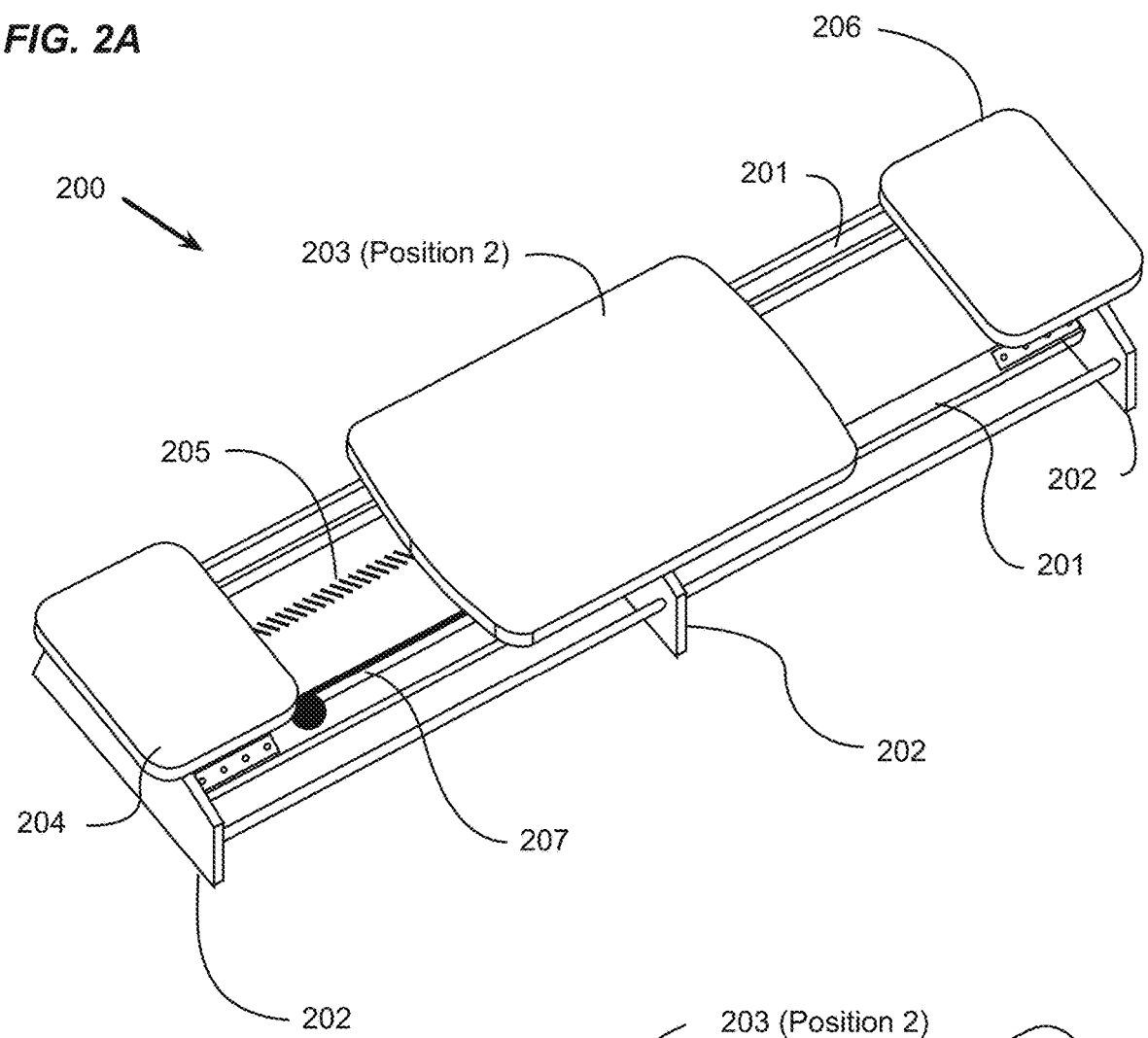
FIG. 2A is an exemplary diagram showing a top three-quarters view of a Pilates apparatus.

FIG. 2A is an exemplary diagram showing a top three-quarters view of a Pilates apparatus 200. More specifically, the primary operable components of a typical Pilates apparatus are shown, including a pair of parallel rails 201 extending substantially the length of a rectangular Pilates structure, the rails being aligned with the longitudinal axis of the apparatus, and affixed to a structure supported by support feet 202. A stationary exercise platform 204 is shown at a first end of the apparatus, and a second stationary exercise platform 206 is shown at a distal second end of the apparatus. Therebetween, a slidable carriage 203 is shown slidable upon the parallel rails, and biased toward the first end by means of one or more removable attachable spring biasing means 205. The spring biasing means provide a resistance force against which an exerciser must overcome in order to move the slidable carriage in a direction towards the second end of the apparatus. U.S. Pat. No. 7,803,095 titled Exercise Machine to Lagree and U.S. Pat. No. 8,641, 585 titled Exercise Machine to Lagree are hereby incorporated by reference herein in their entirety.

Although the structure and operation of a Pilates apparatus is well known to those skilled in the art, it will be noted that a new and novel addition is a sensor 20 to determine the position of the slidable carriage 203. One example of a sensor 20 is a rotary displacement sensor, also referred to as a string potentiometer 207 with a first end affixed to and proximal to the first end of the apparatus structure, and a second end affixed to the slidable carriage 203. As the slidable carriage is moved upon the sliding rails, the string of the string potentiometer unwinds or winds about the pulley of the potentiometer, thereby creating an electrical signal corresponding to the actual position of the slidable carriage. In the drawing, and merely to illustrate the approximate placement of a string potentiometer upon a Pilates apparatus, the slidable carriage 203 is shown in "Position 2", meaning that the carriage has been moved against the spring biasing means from its default starting position.

Figure 2B:
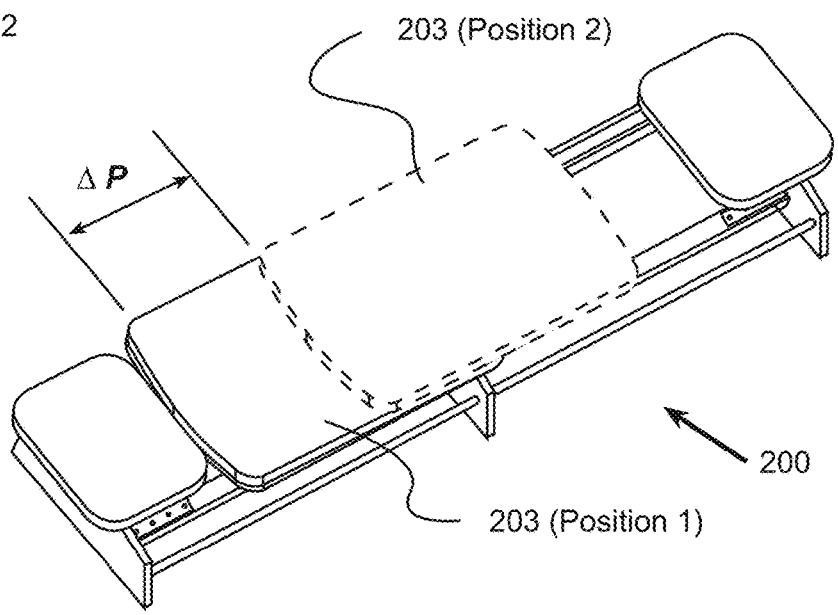
FIG. 2B is an exemplary diagram showing a top three-quarters view of a Pilates apparatus.

FIG. 2B is an exemplary diagram showing a top three-quarters view of a Pilates apparatus 200. More specifically, the slidable carriage 203 is shown in its default position "Position 1", biased toward the first end of the apparatus to which the removably attachable spring biasing means are affixed. Position 1 represents what is often the position of the slidable carriage prior to an exerciser beginning a Pilates exercise.

As previously described in FIG. 2A, the slidable carriage, when in Position 2, is recognized to have moved a certain travel distance Δ P away from Position 1. The travel distance is measured by the string potentiometer not shown, but which was previously described.

It should be noted that for any given exercise there is a theoretically optimal travel distance depending in the height, and correspondingly the range of motion, of any exerciser. Therefore, one important and novel element of the present invention provides for the measurement of the travel distance of the slidable carriage by any exerciser of any height performing any given exercise upon the apparatus.

The measurement of the travel distance of a Pilates slidable carriage therefore provides for the collection of measurement data that for the first time may be used to assess the performance of an exerciser upon a Pilates apparatus.

It should be noted that although the preferred method of measuring the position of a slidable carriage, and further the direction of carriage movement is by use of a high reliability, low cost, and highly precise string potentiometer, any of the foregoing measurement methods may be used provided they meet the production and performance criteria necessary to deliver the performance and economic requirements of the apparatus and instruction process of the present invention.

Figure 3:
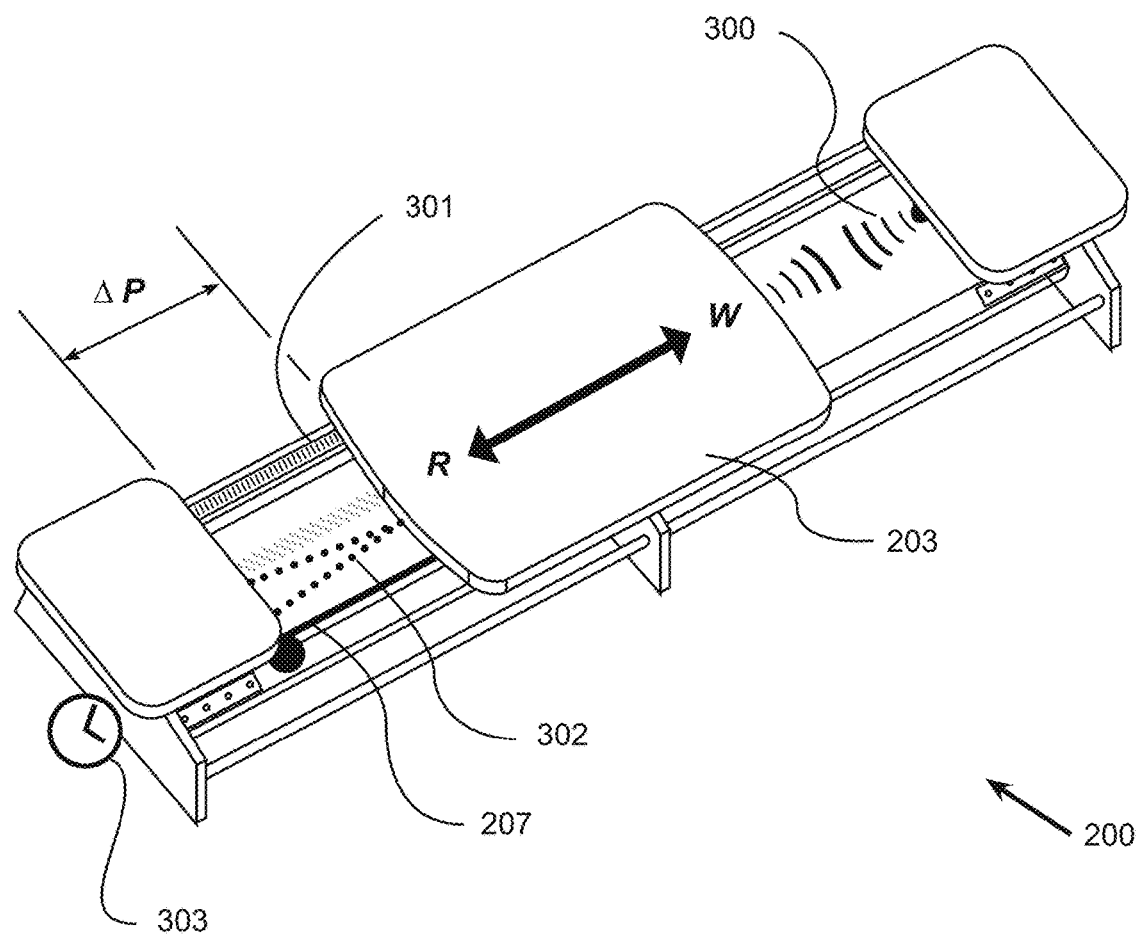
FIG. 3 is an exemplary diagram showing a top three-quarters view of a Pilates apparatus with sensor options.

FIG. 3 is an exemplary diagram showing a top three-quarters view of a Pilates apparatus with sensor options. More specifically, although the string potentiometer as just described is one device that may be used to measure the travel distance of a Pilates apparatus, those skilled in the art will appreciate that other sensors and measuring means may be used in the alternate.

One means of measuring travel distance of a slidable carriage in real time is by acoustic means 300 whereby ultrasonic sound is transmitted from one position, towards a movable object, the distance between the two objects being measured by correlating the wavelength of the transmitted sound to the wavelength of the sound reflected by the targeted object. This distance measurement means is known as the Doppler Effect. Although this method may be used in the present invention, it is more costly than a string potentiometer as previously described, and encounters measurement problems related to traditional materials used on exercise platforms of Pilates apparatuses that are relatively non-reflective of sound waves, and further encounter problems with the distance between the slidable carriage and the first end of the apparatus approach zero.

Distance measurement may also be accomplished using laser measurement 302, however the high speed of a laser pulse is best used at distances longer than the expected normal travel distance of a Pilates carriage, unless highly sensitive and more expensive measurement devices are used. The added expense is not preferred when lower cost production options are available.

A linear displacement sensor 301 may also be used to measure the real-time position of a slidable Pilates carriage. However, linear displacement sensors are typically less reliable over hundreds of thousands of cycles, and are typically more expensive than the preferred string potentiometer.

Further, although real-time position measurement is one function performed by a measurement system and device, use of a timer 303 provides for computation of the speed at which the carriage travels between any two given positions, and further provides for the determination of the direction of carriage movement.

For the first time, speed and direction of a slidable carriage are therefore provided for on an improved Pilates apparatus. Speed and direction are important elements of the system and method of the present invention since proper coaching of an exerciser requires the determination of how efficient the exerciser is working against the resistance bias, determined as the carriage moves away from the first end of the apparatus, and whether the exerciser is completing each repetition within the allotted timeframe.

Those skilled in the art will appreciate the microprocessors provide for a digital clock function, but also that a digital signal from an external clock may be used.

Figure 4:
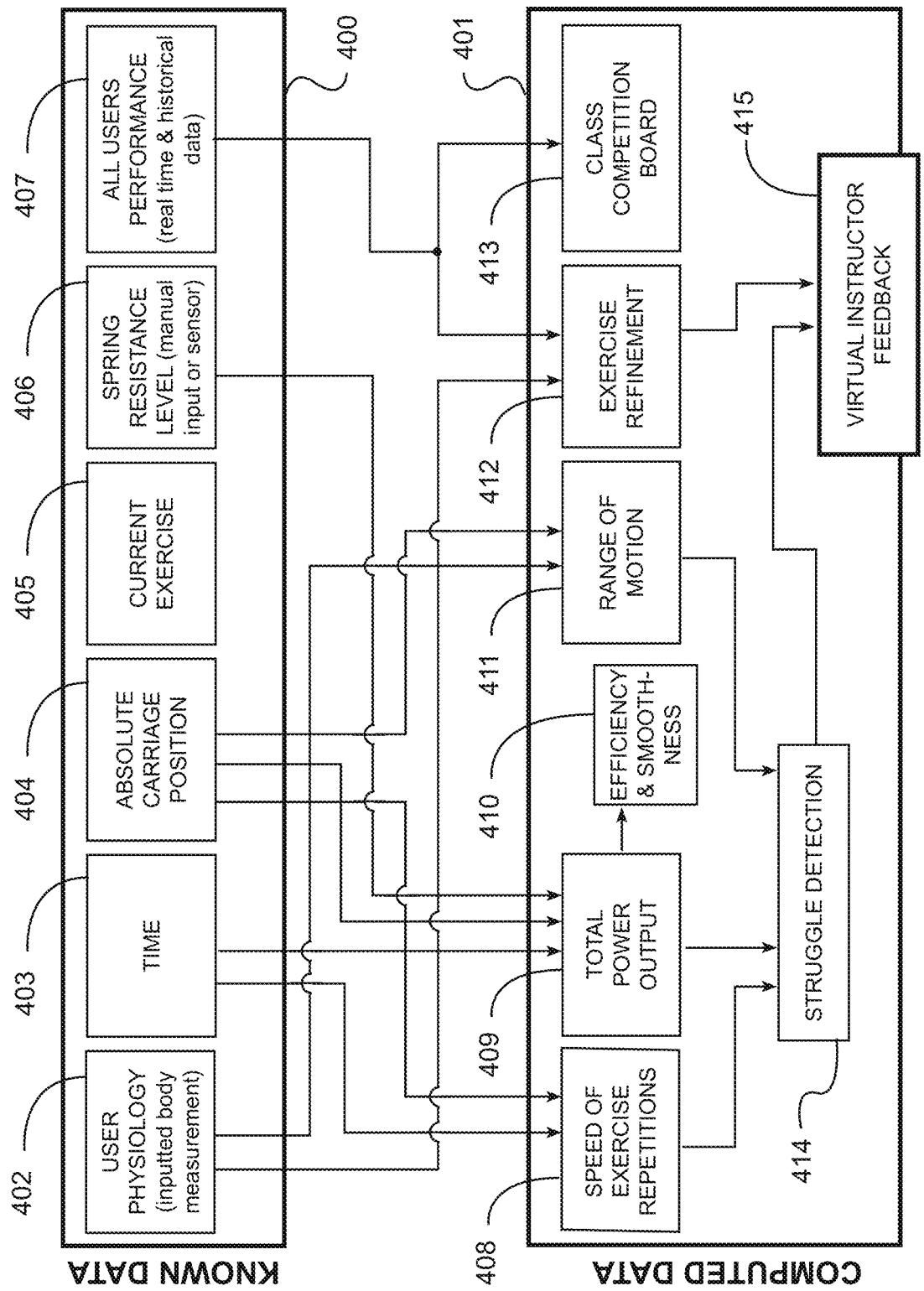
FIG. 4 is an exemplary diagram showing a flow chart of known and computed data components of a virtual Pilates instructor.

FIG. 4 is an exemplary diagram showing a flow chart of known and computed data components of a virtual Pilates instructor which are calculated by a computer processor 10 or similar device. In the system of the present invention, certain data related to the exercise and exercise apparatus are known. Known data 400 is used to compute real-time exercise performance data.

The known data therefore includes user physiology 402, namely the exerciser's height. It is well known that the stride of a tall person is typically much longer than a short person. Similarly, the travel distance of the slidable carriage caused by performance of an exercise by a tall person will typically be longer than the travel distance caused by a short person. Physiological measurement is a key component in determining the proper range of motion 411, and therefore the proper carriage travel distance, for exercisers of any height.

Alternatively, physiological data may include other body measurements, for example, the length of the femur, length of the forearm, length of torso, or the reliable measurement of other body parts that could be considered for determining the proper range of motion while performing exercises on a Pilates apparatus.

As previously discussed, time 403 is a data element used to determine a variety of performance elements including the total power output 409, and speed of exercise repetitions 408. Absolute carriage position 404 is determined by use of a measurement device as previously discussed.

As initially instructed by a live person instructor, or as called for in an exercise routine plan, the exercise to be performed 405 is also known prior to beginning an exercise. There are literally many hundreds of exercises that are typically performed on a Pilates apparatus, the exercise therefore providing to a processor the estimated range of motion information that corresponds to the particular exercise.

Prior to starting an exercise, either via manual or automated means, an exerciser establishes the resistance level 406 against which they will exercise by attaching an appropriate number of springs between the slidable carriage and the stationary first end of the apparatus that correspond to the desired workload, usually expressed in pounds. The spring resistance is used to determine power output, and correspondingly, the estimated calories consumed during the workout session.

Those knowledgeable of the Pilates industry will appreciate that exercisers typically perform Pilates exercises in a class environment in which each exerciser is exercising on their respective apparatus. An exercise class may consist of as few as one individual, or dozens of individual exercisers. As just discussed, certain data is known about the exerciser, time and the apparatus. Within a class environment, all of the data of all of the exercisers performing on all of the apparatuses are also known. Therefore, the performance of all users 407 are known, and may be displayed as a means to inform the live instructor as to exercisers who may need additional assistance, or to provide a performance "leader board" showing the exercisers performing the exercises most efficiently or accurately.

Therefore, with the known data 400 having been established, the present invention provides for computed data 401 to be generated in order to determine exerciser performance.

Pilates classes are conducted for a specific amount of time, and exercise routines are comprised of a plurality of different exercises. Further, each exercise is typically repeated a prescribed number of times before changing to a new exercise. Therefore, one important element of exercise performance is ensuring that every exerciser performs the same number of repetitions within the same allocated time. By using known data time 403 and carriage position 404, the present invention provides for counting the number of repetitions, and further determining whether the repetitions are performed within the prescribed timeframe.

Many exercisers desire to know how many calories they "burned" during an exercise session. The present invention provides for the computation of caloric consumption during a workout session in part, by computing the total power output 409 during the session. By using the known spring resistance 406 in pounds, the carriage position 404 as used to determine the distance over which the pounds were pushed, and the time 403, power can be computed using well known formulae.

Further, as a novel and previously unavailable means of determining exercise efficiency corresponding 410, the present invention provides for the analysis of power output over time by assessing whether the work phase and recovery phase of each work cycle, or repetition, was smooth and consistent, or jerky and erratic.

By further analyzing this new Pilates performance metric against the speed of exercise repetitions 408, the total power output 409, and the range of motion 411, this novel performance metric is a powerful new indicator to determine whether the exerciser is struggling too much 414, or in other words, whether the exerciser may be attempting to work out against too high a resistance, or over-extending their recommended range of motion during exercise.

A live instructor, armed with the previously unavailable information that one or more members of a class are struggling, can immediately stop the exerciser and reduce the resistance level of the spring biasing means, thereby preventing soft tissue or joint injury.

As exhaustively discussed herein, exercising throughout the entire range of motion is a key performance objective if the exercisers are to maximize cardiovascular and strength improvements from an exercise session. Therefore, the actual range of motion 411 for any given exerciser can now be determined with precision by comparing exerciser physiology 402 and the estimated distance they should be able to move the slidable carriage, with the actual carriage position 404. The estimated range of motion is further refined 412 over time by collectively comparing all users' performances against all users' physiological measurements, thereby establishing more accurate mean and average ranges of motions for each exercise based on a larger exerciser cohort.

In some instances, it is desirable to provide a "leader board" that displays the performance of all exercisers within a Pilates class. A class competition board 413 can induce a consciousness among all exercisers to perform higher efficiency and more accurate exercises in order to successfully compete with their peers.

A fundamental aspect of the virtual instructor of the present invention, as previously discussed, is to provide constructive, real-time feedback 415 to each exerciser, the feedback therefore providing for recommendations to improve efficiency, maximize the benefits of the exercise period, and to prevent injuries. The specifics of the feedback, and the methods of delivering feedback to the exerciser are later discussed in more detail.

FIG. 5A is an exemplary diagram showing a side view of a person exercising on a Pilates apparatus. Merely as one illustrative example showing the travel distance of a slidable carriage during an exercise, a representative exerciser 500 is shown on a Pilates apparatus with the right foot placed on the stationary exercise platform 204, and the left foot placed upon the slidable carriage 203. The left illustration shows the exerciser in the starting position, ready to perform the "lunge", an exercise well known in the fitness industry.

Having previously established a predetermined resistance level by attaching resistance springs between the carriage 203 and stationary first end of the apparatus, the exerciser moved the left foot forward, working against the resistance means. In the drawing, it can be readily determined that the exerciser has moved the carriage an actual distance referred to as $\Delta P^1$.

In practice, an exerciser often times does not know when they have pushed the carriage forward far enough, or too far. Therefore, those skilled in the art will appreciate that many exercisers may under-extend the forward foot, and in some cases over-extend the forward foot. They will also appreciate that the actual distance considered ideal for a tall person will be a larger dimension when compared to a shorter person.

It is therefore desirable to inform the exerciser, in real time, and while they are performing the lunge, when they have achieved the ideal estimated carriage travel distance.

FIG. 5B is an exemplary diagram showing an illustration and chart to determine estimated range of motion. More specifically, in order to determine the estimated ideal range of motion for an exerciser, the present invention provides for a mathematical formula to be applied to known physiological dimensions of the exerciser.

In the drawing, the exerciser's height is shown as D1, while the estimated carriage travel distance is shown as D2.

In the chart 501, representative of a database containing a plurality of exercises and corresponding formulae for converting a physiological measurement to a corresponding carriage travel distance, an exercise 502 is listed as one of the exercises to be performed. Upon inputting of the physiological measurement 503 of the exerciser into the system of the present invention, the estimated ideal carriage travel distance for that particular exerciser, and for that particular exercise is retrieved from a lookup table 504, the data in the lookup table having been previously inputted.

As yet another means of estimating the carriage travel distance based on a physiological measurement, a ratio formula may be applied to the physiological measurement 503, thereby resulting in a corresponding dimension for the estimated travel distance. This method of computing the estimated travel distance may be applied equally and accurately to any physiological measurement of any exerciser whether their actual measurement is contained in a lookup table.

Further, by incorporating other known data not previously discusses, that data comprising gender, age, or known medical conditions that may impact the estimated normal range of motion, alternate ratios can be incorporated into the present invention. This preferred method results in a significant reduction in time and expense in building a relational database comprising physiological measurements, estimated carriage travel dimensional, and modifications accounting for age, gender or other parameters, especially when considering that literally hundreds of exercises may be inputted into the database.

Figure 6A:
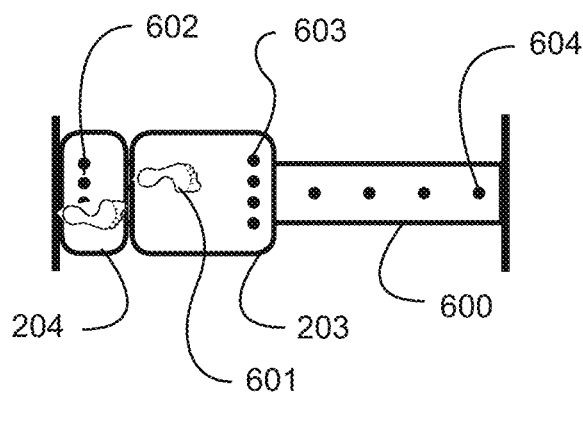
FIGS. 6A and 6B are exemplary diagrams showing top views of a Pilates apparatus with an instructional feedback system.
Figure 6B:
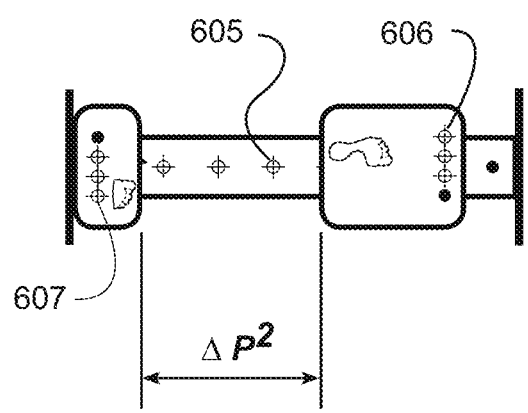

FIGS. 6A and 6B are exemplary diagrams showing top views of a Pilates apparatus with an instructional feedback system. More specifically, FIG. 6A shows a top view of a Pilates apparatus comprising a monorail 600, although a pair of parallel rails as previously described may be used. Further, the drawing shows a slidable carriage 203 and a stationary exercise platform 204 at a first end. Footprints 601 represent the approximate foot positions of an exerciser not shown readying to perform a "lunge" exercise.

As will be further described, illuminated and non-illuminated lights are shown in the drawing, the purpose of which is to guide an exerciser's movement of the slidable carriage to a position estimated to correspond to the exerciser's unique range of motion for this exercise.

Since the hypothetical exerciser has yet to start the exercise, three series of lights 602, 603, 604 are all shown as not being illuminated. Three series of lights are shown merely for example, and only one series of lights may be preferred. Further, only four lights are shown in each of the series, but the number of lights are not meant to be limiting, and any number of lights may be used.

With a left foot 601 placed upon the slidable carriage, the exerciser begins the exercise by pushing the left foot towards the second of the apparatus. As one example of how lights guide the exerciser to move their left foot to the estimated ideal stopping point, the stopping point corresponding to the estimated full extension of their range of motion for this exercise, lights 605, 606, 607 are sequentially illuminated as the carriage moves away from the first end. As can be readily seen, the lights illuminate until the carriage travels to an estimated maximum distance from the first end, the distance correlating to the range of motion limit.

In the drawing, the estimated range of motion limit is shown as $\Delta P^2$, the point of left foot forward extension to which the exerciser should aspire to achieve at the mid-point of each exercise repetition.

As one example of correlating illuminated lights to carriage position, each series of lights would represent the total possible travel distance of a slidable carriage of the apparatus. As the carriage is moved from its exercise starting position, lights would illuminate in a sequence corresponding to the actual carriage position relative to the total possible travel, with the illumination sequence terminating when the carriage reached the estimated ideal position for the exerciser.

As one example of correlating illuminated lights to carriage position, a series of lights may all be non-energized at the start of the exercise, and upon first movement of the carriage, begin to blink on and off at a slow rate. As the carriage continues moving distal to the first end of the apparatus, the blinking frequency increases until the lights illuminate without blinking. The steady illumination of all of the lights in a series would indicate to the exerciser that the proper range of motion has been reached, and that the exerciser should start to reverse the direction of the carriage movement back toward the first end of the apparatus to complete one repetition.

As can readily be understood, lights may be always illuminated in a green color, and change colors during movement, ultimately stopping the color change when they are red, indicating that the proper range of motion has been reached by the exerciser.

The foregoing examples of lighting series being used as a visual means to instruct an exerciser to move to the optimum range of motion, whether based on sequential illumination, changing frequency rate of blinking, color changes, or a combination thereof, the examples are not meant to be limiting, and any method of using lights as an instruction related to exerciser range of motion upon a Pilates apparatus maybe used without deviating from the spirit and intention of the novel instruction system and method of the present invention.

FIG. 7 is an exemplary diagram showing real time analysis and feedback related to range of motion. As would be expected from a live person instructor, the automated instruction method of the present invention provides considerable more information and direction than merely illuminating lights corresponding to the range of motion.

In the chart 700, various methods of exerciser feedback 702 are detailed relating to two of a plurality of actual exercise conditions. A first condition is created when an exerciser stops the forward foot movement and, correspondingly the forward travel of the slidable carriage prior to reaching the estimated optimal position. Namely, the exerciser has moved the carriage five inches 701 shorter than the estimated ideal, the "−5" shown as the deviation between the estimated ideal position, and the exerciser's actual position of the carriage. The result of not extending to the full range of motion is a diminished efficiency of the workout that will result in slower fitness development.

The feedback column 702 corresponding to this condition contains information of varying format and content which is not meant to be limiting, but includes:

a) General textual information that may be displayed on a display screen 30 or audibly delivered as a prerecorded or computer generated voice message, b) Instructions to extend the forward foot further on the next repetition, the instructions being displayed on a display screen or audibly delivered as a prerecorded or computer generated voice message, c) A condition change in one or more lights and/or series of lights as previously described, d) An audible alert such as a tone or frequency change that correlated to an instruction to extend the forward foot an additional distance,
e) A tactile feedback that may include a vibration, or a frequency change to vibration of one or more of the exercising platforms of the apparatus by a tactile feedback device 50,
f) A combination of any of the above.

A second condition is created when an exerciser extends the forward foot movement beyond the estimated ideal range of motion. Namely, the exerciser has moved the carriage two inches 703 shorter than the estimated ideal, the "+2" shown as the deviation between the estimated ideal position, and the exerciser's actual position of the carriage. The result of extending beyond the full range of motion is an increase in the likelihood of joint or soft tissue injury, and an increase in difficulty in maintaining a rapid repetition cycle time as prescribed by the exercise routine.

The feedback column 704 corresponding to this condition therefore contains a plurality of information unique to rectify this condition, the information not meant to be limiting, but includes:
a) General textual information that may be displayed on a display screen 30 in communication with the computer 10 or audibly delivered via a speaker 40 in communication with the computer 10 as a prerecorded or computer generated voice message,
b) Instructions to extend the forward foot further on the next repetition, the instructions being displayed on a display screen or audibly delivered as a prerecorded or computer generated voice message,
c) A condition change in one or more lights and/or series of lights as previously described,
d) An audible alert such as a tone or frequency change that correlated to an instruction to extend the forward foot an additional distance,
e) A tactile feedback that may include a vibration, or a frequency change to vibration of one or more of the exercising platforms of the apparatus,
f) A combination of any of the above.

As will be instantly appreciated by those skilled in the art, the system and method of instructing an exerciser as to the proper carriage travel distance for their unique physiological measurements for a particular exercise, and that further provides real-time instructions related to corrective actions to improve exercise form on subsequent repetitions of the exercise, whether through various visual, audible or tactile means.

FIG. 8 is an exemplary diagram showing real time analysis and feedback related to exercise speed. As previously discussed, maintaining a properly timed repetition cycle throughout an exercise sequence is important component of maximizing the fitness benefits desired by exercisers. Therefore, analysis of actual repetition speed of an exerciser relative to the estimated ideal repetition speed provides for further instruction by be given to the exerciser that falls off of the repetition cycle rate.

In the chart 800, a first condition of an exerciser exercising too slowly is shown. In the deviation column 801, it can be readily seen that the exerciser completed on repetition in 4.60 seconds, or 0.6 seconds slower than the estimated ideal time. Therefore, feedback instructions center on coaching the exerciser to speed up their repetition cycle.

As previously described in FIG. 7 with respect to instructions related to the range of motion, the feedback corresponding to a condition of slow exercise repetitions therefore contains various instructional feedback intended to rectify this condition of exercising too slowly, the information not limited to, but including for example:
a) General textual information that may be displayed on a display screen 30 or audibly delivered as a prerecorded or computer generated voice message,
b) Instructions to extend the forward foot further on the next repetition, the instructions being displayed on a display screen 30 or audibly delivered as a prerecorded or computer generated voice message,
c) A condition change in one or more lights and/or series of lights as previously described,
d) An audible alert such as a tone or frequency change that correlated to an instruction to extend the forward foot an additional distance,
e) A tactile feedback that may include a vibration, or a frequency change to vibration of one or more of the exercising platforms of the apparatus,
f) A combination of any of the above.

In the chart 800, a second condition of an exerciser completing a repetition too quickly is shown. In the deviation column 802, it can be readily seen that the exerciser completed on repetition in 3.15 seconds, a considerable 0.85 seconds faster than the estimated ideal time. Therefore, feedback instructions center on coaching the exerciser to slow their repetition cycle.

So as not to be unduly burdensome, the list of possible methods of feedback to the exerciser are not repeated, but it should be readily understood that feedback may be in the form of visual, audible, or tactile feedback means, or a combination thereof as previously described.

FIG. 9 is an exemplary diagram showing real time analysis of exercisers on a plurality of apparatuses within an exercise facility. It is often desirable to display fitness performance information as a means to motivate participants to perform better. The chart 900 illustrates comparative performance information that may be displayed showing certain computed data of twelve participants in a Pilates class.

Further, it is desirable to display instructional information to better inform class participants about the current exercise, upcoming exercises, the elapsed exercise time, or other metrics related to the exercise session. In the chart, the exercise name and repetition number 901 are displayed as a means to inform exercisers that they are to perform five more repetitions of the "lunge" before changing to a new exercise in the routine.

Scoreboards and leader boards are a well-known means to display relative ranking of competitors during a sports event, for example, golf and basketball games, and tennis tournaments. However, no such leader boards have been found in Pilates studios since no method of assessing performance of Pilates exercisers has been available to drive the competitive performance information.

The novel system of the present invention provides for displaying data received from a plurality of apparatuses 902 in a Pilates studio or gym facility, and further provides for the performance ranking 903 of participants performing on the apparatuses.

Although the columns of the chart 900 highlight various known and computed data corresponding to the performance of each of the class participants, the data points shown are not meant to be limiting, and any known or computed data may be displayed.

It should be noted that a live person instructor typically presides over each Pilates class, but as previously discussed, instructors are ill-equipped to monitor the real-time performance of every class participant. The chart therefore provides the live instructor with important real-time information, for instance, that participants on machine numbers 5 and 9 are struggling 904, and may need immediate help. A struggle alert displayed by the present invention indicates, as one possible cause of the exercisers' problem, that the resistance level on their apparatuses may have been set too high. Having been alerted to the extraordinary effort of the two exercisers just described, the live instructor can immediately reduce the resistance level on the two just-mentioned apparatuses by simply detaching one spring. Without the new and novel exerciser performance information now made possible by the present invention, the two exercisers just mentioned would have unduly struggled throughout the exercise session, possibly overexerting muscles or sustaining injury.

Therefore, those skilled in the art will appreciate that exercise performance feedback is not only important information useful to Pilates exercisers who endeavor to improve their fitness levels, but the newly available information is also highly valuable to live person instructors as a means to identify, with precision, which exercisers require the additional help or assistance of a live instructor.

FIG. 10 is an exemplary diagram 1000 showing a block diagram of network features. In the drawing, various features of the novel system and method of the present invention provide for easy operation and management of one or more improved Pilates apparatuses on a network.

Methods of transmitting data from a plurality of electronic devices to a network server are well known to those skilled in the art. For efficiency, the exhaustive detail of the well-known art of network communications, whether via Bluetooth, WI-FI or other wired means are not discussed. Nevertheless, certain novel features of the present invention are beneficial.

A remote control 1001 provides a means for a live instructor to communicate with a plurality of apparatuses simultaneously, namely by delivering information to at least one processor on each apparatus that may, for example, include the exercise name. As previously discussed, the range of motion that each exerciser should achieve is defendant, in part, on knowing what exercise is being performed. In the event that an entire routine of different exercises is not preprogrammed into the network, a remote control as just described is a preferred means of simultaneously communicating the exercise name, as well as other information, to one or more apparatuses on a network.

It is also beneficial to ensure that all apparatuses on the network are operating properly. The present invention provides for network-wide diagnostics 1002 wherein the operation, settings, or other information related to one or more network devices may be tested for operation within defined parameters.

It is also preferred that a live person instructor be provided with real-time information regarding the performance of all exercisers on all apparatuses in communication with the network, and more specifically, to receive alerts 1003 regarding which exercisers require immediate help.

The features of the network of the present invention are not meant to be limiting, and are merely presented as examples of three novel management and operations features of the virtual instructor that may be conducted over a network.

FIG. 11 is an exemplary diagram showing a representative post-exercise report of one exerciser. It is well known that exercisers prefer to review and analyze their performance periodically as a means to determine progress towards a fitness goal. Runners and bicyclists are just two groups of exercisers benefitting from technology that tracks, and later reports an exerciser's performance during a workout session. Unfortunately, without the collection and analysis of Pilates exercise performance data as provided by the present invention, Pilates exercisers cannot enjoy the benefit of a definitive post-workout performance summary.

In the drawing, a performance review of the exerciser using one particular apparatus 1100 in a Pilates studio or gym facility may be provided in a digital or paper form. The review summarizes a plurality of performance metrics unique to the exerciser and exercise session just completed, the metrics including, but not being limited to the total exercise time 1001, range of motion accuracy 1102, special alerts or warnings 1003 related to their workout session, and preferably, an automatically generated list of instructions 1104 that will help the exerciser to improve their performance during the next exercise session they participate in.

Therefore, those skilled in the art will appreciate the benefit of providing an exerciser with objective, calculable information related to their performance during a Pilates exercise, and will further appreciate the commercial value of such a new and novel system, especially when considering the competitive advantages provided by the present invention when compared to traditional Pilates apparatuses that are incapable of tracking or reporting on an exerciser's performance.

As will become immediately obvious to one skilled in the art, the collection and analysis of known and computed data related to exercising on an improved Pilates apparatus of the present invention provides for more effective monitoring and coaching of exercisers during a Pilates exercise session, aids in reducing exerciser injury, and enhances the exerciser's ability to self-manage their workout intensity and efficiency. Further, within a highly competitive Pilates industry, skilled artisans will recognize the commercial value of the improved system and method of instructing Pilates exercisers.

Figure 12A:
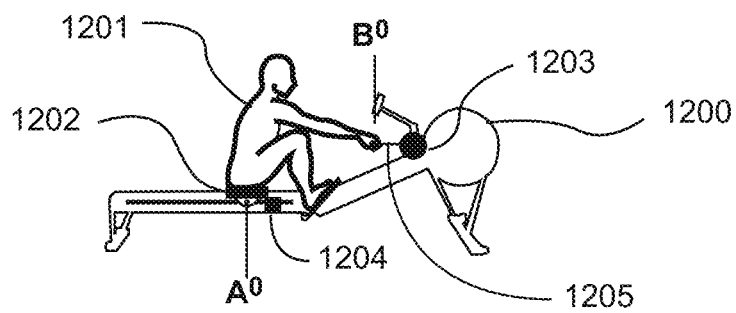
FIG. 12A is an exemplary diagram showing a side view of representative exerciser at the start of a rowing machine exercise.

FIG. 12A is an exemplary diagram showing a side view of representative exerciser at the start of a rowing machine exercise. Rowing machines intended to simulate rowing of a scull or working shell are well known in the industry. However, one widely recognized problem with rowing machines is that the apparatuses allow exercisers to overextend their normal range of motion, and provide no feedback with regard to the distance an exerciser should push the seat back with their legs, and more importantly, what distance the exerciser should pull the pull handle towards them during exercising.

As one variation of the present invention, a plurality of sensors are affixed to the apparatus. More specifically, one sensor 1203 is affixed to apparatus in such a manner as to measure travel of the seat 1204 of a rowing machine, as it closely correlates to the slidable carriage of a Pilates apparatus, and a second sensor 1204 is affixed to the apparatus to measure travel of the pull rope 1205.

Generally, a rowing machine apparatus comprises a resistance flywheel 1200 to which a pull rope 1205 is attached. An exerciser 1201 sits upon a sliding seat 1202 slidable along one or more rails aligned with the longitudinal axis of the apparatus. At the beginning of an exercise, the handles of the exerciser grasp a handle of the pull rope while seated as shown, with the feet positioned upon foot platforms against which the exerciser will push during exercising. At the start of an exercise, the seat is positioned at a "zero" point shown as $A^0$. At this point, the arms are fully extended, while the knees are bent, allowing the seat to position as closely as possible to the flywheel end 1200 of the apparatus.

Figure 12B:
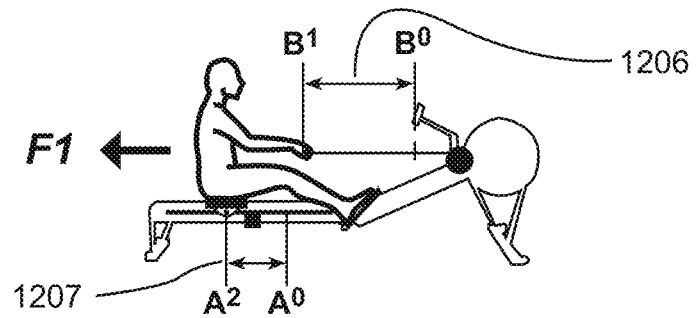
FIG. 12B is an exemplary diagram showing a side view of representative exerciser at the "catch" phase of a rowing machine exercise.

FIG. 12B is an exemplary diagram showing a side view of representative exerciser at the "catch" phase of a rowing machine exercise. As the exerciser begins straightening their legs, thereby pushing the seat with a force F1 from a first position $A^0$ to a second variable position $A^2$, they simultaneously begin to pull their hands towards their chest, thereby increasing the amount of pull rope played out by the rope windings on the flywheel 1200. As may be readily seen, the distance that the pull rope travels between starting position $B^1$ and intermediate position $B^2$ is greater than the distance that the seat travels at this stage of the exercise.

It should be noted that the travel distance relationship between the pull rope and the seat are critically important to properly performing the exercise, and that the relationship varies throughout each repetition of the exercise. It should also be noted that those skilled in the art will appreciate that no rowing machine apparatuses currently provide for continuous, real-time analysis of pull rope versus seat travel during an exercise. It should also be noted that as the travel distance of the pull rope 1206 is typically greater than the travel distance of the seat 1207 throughout the exercise, the speed of travel differ between the pull rope and seat. However, traditional rowing machine apparatuses fail to measure the relative distances, do not analyze the travel ratios through the pull cycle, and do not provide feedback to exercisers as to corrective measures they should take to ensure proper form and performance of the exercise.

Figure 12C:
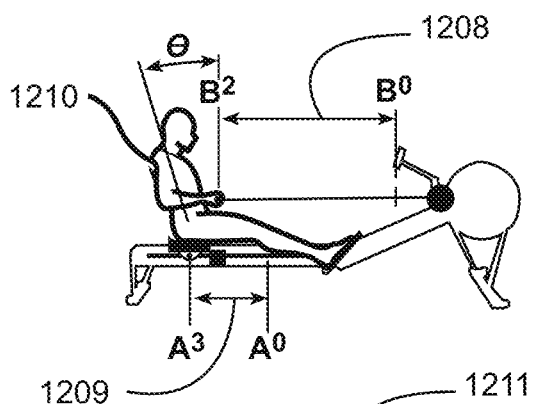
FIG. 12C is an exemplary diagram showing a side view of representative exerciser at the "full pull" phase of a rowing machine exercise.

FIG. 12C is an exemplary diagram showing a side view of representative exerciser at the "full pull" phase of a rowing machine exercise. In the drawing, the exerciser has reached a position wherein their legs are fully extended, indicating the maximum leg range of motion, and correspondingly the maximum seat travel 1209 between starting position $A^0$ and maximum position $A^3$. It should be noted that this travel distance is relative to the physiological measurements of the exerciser. More specifically, a taller person will push the seat a greater distance from the flywheel end of the apparatus as compared to a shorter person.

Correspondingly, the exerciser has pulled the rope pull handle fully towards the body, creating nearly the maximum pull distance 1208 between the starting point $B^0$ and full-pull position $B^2$.

However, as can been seen in the illustration, the exerciser's back 1210 has been extended slightly away from the flywheel end at an angle θ, thereby extending the pull rope an additional short distance beyond the full-pull position when their hands are fully against their body. Those skilled in the art suggest that the back should angle away from the flywheel end at approximately 25 to 35 degrees from the vertical as shown.

Figure 12D:
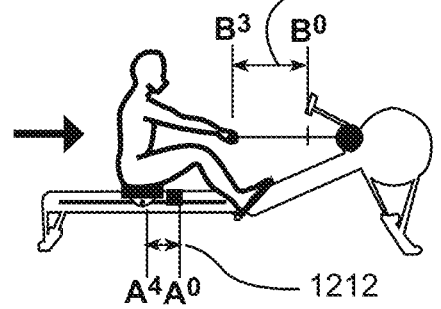
FIG. 12D is an exemplary diagram showing a side view of representative exerciser beginning the recovery phase of a rowing machine exercise.

FIG. 12D is an exemplary diagram showing a side view of representative exerciser beginning the recovery phase of a rowing machine exercise. In the drawing, the exerciser is engaging on the recovery phase of the repetition, having completed the full-pull extension. As previously described, the travel speed and distance of the pull rope 1211 and seat 1212 still differ by a variable, yet predictable ratio.

Figure 12E:
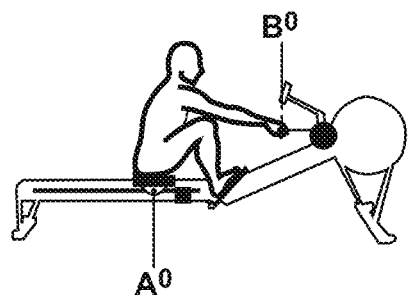
FIG. 12E is an exemplary diagram showing a side view of representative exerciser returned to the starting position after completing one repetition of a rowing machine exercise.
Figure 14:
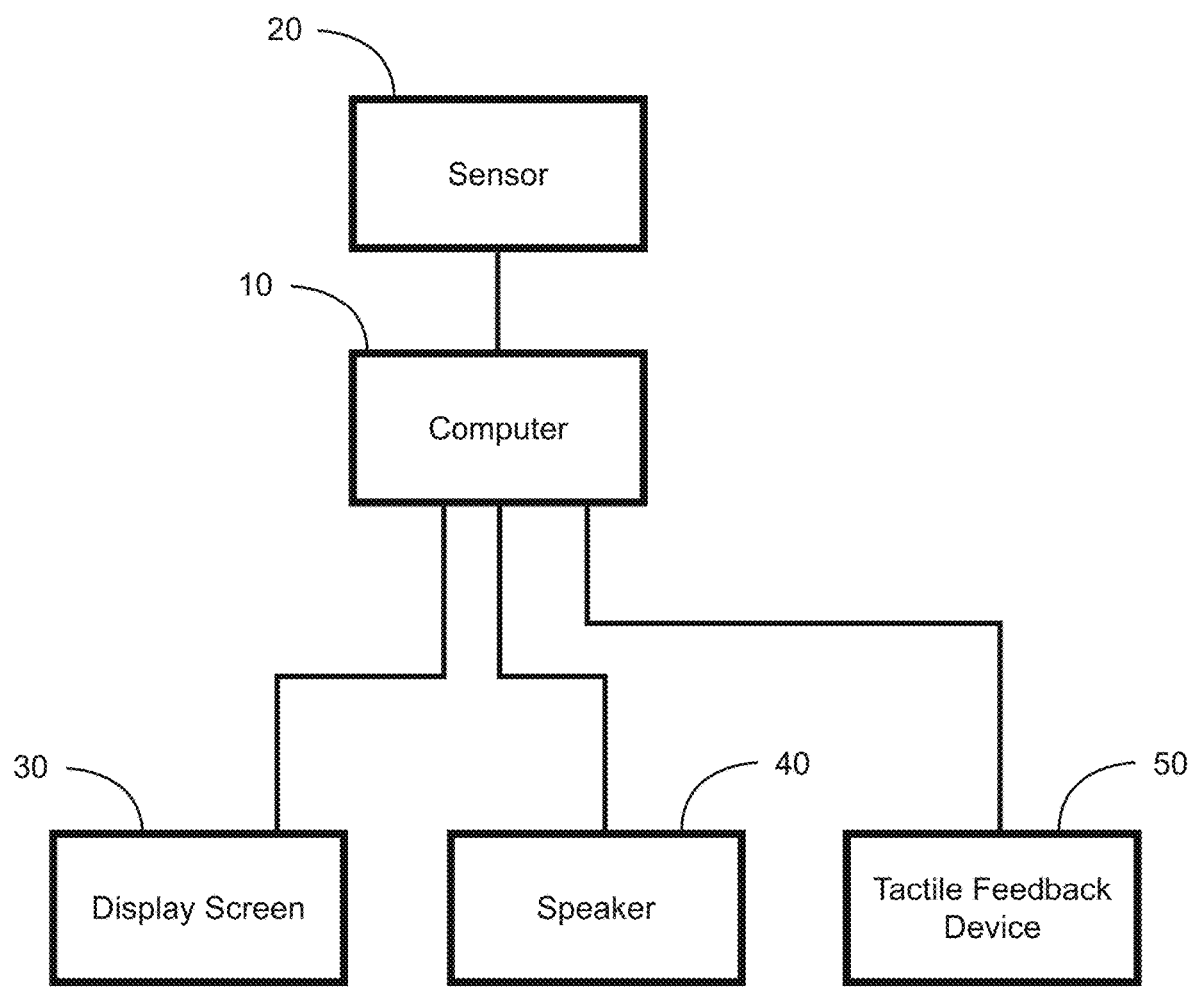
FIG. 14 is a block diagram illustrating the various electronic devices in communication with one another.

FIG. 12E is an exemplary diagram showing a side view of representative exerciser returned to the starting position after completing one repetition of a rowing machine exercise. More specifically, the exerciser has returned to the starting point after completing one repetition of the exercise, the seat being returned to the starting position $A^0$ and the pull rope being returned to its starting position $B^0$.

Having completed a full repetition, a summary of the exerciser's performance can be computed including, but not limited to efficiency and accuracy of the work cycle based on the exerciser's physiological measurements, relative travel distance of the pull rope and seat, the total travel as it relates to the recommended range of motion, and the total work performed as expressed in calories, based on a known resistance load of the flywheel resistance means.

FIG. 13 is an exemplary diagram showing anthropometric models and measurements correlating to range of motion. More specifically, anthropometric measurements for the U.S. population are well known, and are based on mean and average measurements of various age groups and genders. So as not to obscure the application of physiological measurements to rowing exercise range of motion, the volumes of data relating to such measurements are not illustrated. However, it should be noted that the application of generally accepted measurement data may be used in the formulae in determining the preferred range of motion estimated for different exercisers.

It is preferred that certain body measurements are more useful in estimating range of motion on a rowing machine. In the drawing, a front view of a representative body 1300 is shown, and includes call outs for body height D3, leg length D5, and torso length D4. In the side view 1301, a specific call out for arm length D6 is shown.

For purposes of illustrating the variation of the present invention as applied to rowing apparatuses, an over-simplified description correlating the body part measurements just described is shown.

A first chart 1302 illustrates possible methods of estimating seat travel preferably using measurements related to height D3, and leg length D5. The determination of the estimated seat travel based on one or both of these measurements can be a pre-inputted lookup table correlating every reasonable height to estimated maximum seat travel, or a computed seat travel distance based on a formula correlating height to estimated travel distance.

A second chart 1303 illustrates possible methods of determining estimated rope travel preferably using measurements related to body height D3, torso length D4, and arm length D6. As will be appreciated by those familiar with rowing physiology, there exists many methods of correlating the measurements just described with the estimated optimal range of motion associated with a full-pull. For purposes of illustrating rope travel estimates, three methods are shown.

The estimated rope travel can be a function of looking up pre-inputted data in a database correlating height to estimated seat travel.

As an alternate means, the estimated rope travel may be a computed distance based solely on height, correlating height to arm length using a predetermined ratio, then further using a formula that incorporates the estimated rope travel as a function of leg length and the distance the seat is moved during the exercise cycle, and further using a trigonometric formula that computes the added longitudinal pull distance based on a defined θ.

As yet another alternate means, having determined the estimated seat travel in the chart 1302, the rope travel may be estimated by applying a ratio to seat travel that corresponds to rope travel.

As can readily be seen, there are myriad methods of estimating the respective rope and seat travel for optimum range of motion for persons of different physiological measurements, and the methods just described are not meant to be limiting.

Further, as described in the Range of Motion FIG. 7 and Repetition Speed FIG. 8, the present invention, after computing actual exerciser performance against the estimated optimal performance parameters for a rowing machine, would provide instruction and feedback to the exerciser, the methods of feedback being one or more of visual, audible or tactile means as previously described.

The functionality provided by the application of the present invention to improved rowing machines therefore provides, for the first time, a system and method to measure independent rope and seat travel upon a rowing exercise machine to determine exerciser form, efficiency, and performance through a proper range of motion.

In addition to Pilates machines and rowing machines, the present invention may be utilized with various other exercise machines such as, but not limited to, weight lifting machines, treadmills and the like.

Any and all headings are for convenience only and have no limiting effect. Unless otherwise defined, all technical and scientific terms used herein have the same meaning as commonly understood by one of ordinary skill in the art to which this invention belongs. Although specific terms are employed herein, they are used in a generic and descriptive sense only and not for purposes of limitation. All publications, patent applications, patents, and other references mentioned herein are incorporated by reference in their entirety to the extent allowed by applicable law and regulations.

The data structures and code described in this detailed description are typically stored on a computer readable storage medium, which may be any device or medium that can store code and/or data for use by a computer system. This includes, but is not limited to, magnetic and optical storage devices such as disk drives, magnetic tape, CDs (compact discs), DVDs (digital video discs), and computer instruction signals embodied in a transmission medium (with or without a carrier wave upon which the signals are modulated). For example, the transmission medium may include a telecommunications network, such as the Internet.

At least one embodiment of the exercise machine monitoring and instruction system is described above with reference to block and flow diagrams of systems, methods, apparatuses, and/or computer program products according to example embodiments of the invention. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, or may not necessarily need to be performed at all, according to some embodiments of the invention. These computer-executable program instructions may be loaded onto a general-purpose computer, a special-purpose computer, a processor, or other programmable data processing apparatus to produce a particular machine, such that the instructions that execute on the computer, processor, or other programmable data processing apparatus create means for implementing one or more functions specified in the flow diagram block or blocks. These computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram block or blocks. As an example, embodiments of the invention may provide for a computer program product, comprising a computer usable medium having a computer-readable program code or program instructions embodied therein, said computer-readable program code adapted to be executed to implement one or more functions specified in the flow diagram block or blocks. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks. Accordingly, blocks of the block diagrams and flow diagrams support combinations of means for performing the specified functions, combinations of elements or steps for performing the specified functions, and program instruction means for performing the specified functions. It will also be understood that each block of the block diagrams and flow diagrams, and combinations of blocks in the block diagrams and flow diagrams, can be implemented by special-purpose, hardware-based computer systems that perform the specified functions, elements or steps, or combinations of special-purpose hardware and computer instructions.

The present invention may be embodied in other specific forms without departing from the spirit or essential attributes thereof, and it is therefore desired that the present embodiment be considered in all respects as illustrative and not restrictive. Many modifications and other embodiments of the exercise machine monitoring and instruction system will come to mind to one skilled in the art to which this invention pertains and having the benefit of the teachings presented in the foregoing description and the associated drawings. Therefore, it is to be understood that the invention is not to be limited to the specific embodiments disclosed and that modifications and other embodiments are intended to be included within the scope of the appended claims. Although methods and materials similar to or equivalent to those described herein can be used in the practice or testing of the exercise machine monitoring and instruction system, suitable methods and materials are described above. Thus, the exercise machine monitoring and instruction system is not intended to be limited to the embodiments shown, but is to be accorded the widest scope consistent with the principles and features disclosed herein.

What is claimed is:

1. An exercise machine, comprising:
   a rail;
   a carriage movably positioned upon the rail, wherein the carriage is adapted to move in a reciprocating manner upon the rail;
   a first sensor that continuously detects a position of the carriage between a first position and a second position, wherein the first sensor transmits a position data in real-time corresponding to the position of the carriage on the rail;
   a processor in communication with the first sensor to receive the position data from the first sensor related to a position of the carriage, wherein the processor is adapted to calculate a state of the carriage based on the position data received in real-time; and
   a feedback device in communication with the processor, wherein the processor controls the feedback device to provide real-time instruction to an exerciser when using the exercise machine on how to adjust their workout.

2. The exercise machine of claim 1, wherein the state of the carriage is comprised of a real-time velocity of the carriage.

3. The exercise machine of claim 1, wherein the state of the carriage is comprised of a real-time velocity of the carriage, wherein the feedback device provides feedback to the exerciser to decrease a velocity of the carriage if the real-time velocity of the carriage exceeds a maximum target velocity.

4. The exercise machine of claim 1, wherein the state of the carriage is comprised of a real-time velocity of the carriage, wherein the feedback device provides feedback to the exerciser to increase a velocity of the carriage if the real-time velocity of the carriage falls below a minimum target velocity.

5. The exercise machine of claim 1, wherein the state of the carriage is comprised of a real-time position of the carriage.

6. The exercise machine of claim 1, wherein the state of the carriage is comprised of a real-time position of the carriage, wherein the feedback device provides feedback to the exerciser to decrease a distance between the first position and the second position if the distance between the first position and the second position exceeds a maximum target distance.

7. The exercise machine of claim 1, wherein the state of the carriage is comprised of a real-time position of the carriage, wherein the feedback device provides feedback to the exerciser to increase a distance between the first position and the second position if the distance between the first position and the second position falls below a minimum target distance.

8. The exercise machine of claim 1, wherein the processor calculates a real-time cycle rate between the first position and the second position during an exercise, wherein the feedback device provides feedback to the exerciser to decrease their cycle rate if the real-time cycle rate exceeds a maximum target cycle rate.

9. The exercise machine of claim 1, wherein the processor calculates a real-time cycle rate between the first position and the second position during an exercise, wherein the feedback device provides feedback to the exerciser to increase their cycle rate if the real-time cycle rate falls below a minimum target cycle rate.

10. The exercise machine of claim 1, wherein the first sensor is comprised of a string potentiometer connected to the carriage.

11. The exercise machine of claim 1, wherein the first sensor is comprised of an acoustic sensor.

12. The exercise machine of claim 1, wherein the first sensor is comprised of a laser sensor.

13. The exercise machine of claim 1, wherein the first sensor is comprised of a linear displacement sensor.

14. The exercise machine of claim 1, wherein the feedback device comprises a speaker that provides audible feedback to the exerciser.

15. The exercise machine of claim 1, wherein the feedback device is comprised of a tactile feedback device that provides tactile feedback to the exerciser.

16. The exercise machine of claim 1, wherein the feedback device comprises a display screen that displays a visual real-time instruction to the exerciser on how to adjust their workout.

17. The exercise machine of claim 1, wherein the feedback device comprises a display screen that displays a visual real-time instruction to the exerciser on how to adjust their workout, wherein the visual real-time instruction is comprised of textual information.

18. The exercise machine of claim 1, wherein the feedback device is comprised of at least one light.

19. The exercise machine of claim 1, wherein the feedback device is comprised of a plurality of lights.

20. The exercise machine of claim 19, wherein the plurality of lights are attached to the carriage.

21. The exercise machine of claim 19, further comprising a first stationary platform connected near a first end of the rail, wherein the plurality of lights are attached to the first stationary platform.

22. The exercise machine of claim 19, wherein the plurality of lights are attached to the rail.

23. The exercise machine of claim 19, wherein the plurality of lights are in series.

24. The exercise machine of claim 19, wherein the real-time instruction is comprised of the plurality of lights blinking at a faster rate or a slower rate to indicate to the exerciser to adjust their speed.

25. The exercise machine of claim 19, wherein the real-time instruction is comprised of the plurality of lights changing color to indicate to the exerciser to adjust their speed.

26. The exercise machine of claim 19, wherein the real-time instruction is comprised of the plurality of lights blinking to indicate to the exerciser to move the carriage and not blinking to indicate to the exerciser to stop moving the carriage.

27. The exercise machine of claim 19, wherein the real-time instruction is comprised of the plurality of lights that change color to indicate to the exerciser to move the carriage and when to stop moving the carriage.

28. The exercise machine of claim 19, wherein the real-time instruction is comprised of the plurality of lights that change color to indicate to the exerciser to move the carriage, when the carriage is approaching an ideal range of motion and when to stop moving the carriage.

29. The exercise machine of claim 19, wherein the plurality of lights are within the rail and are sequentially illuminated as the carriage moves away from a first end of the rail.

30. The exercise machine of claim 19, wherein the plurality of lights are sequentially illuminated as the carriage moves away from a first end of the rail.

31. The exercise machine of claim 19, wherein the plurality of lights are sequentially illuminated until the carriage travels to a desired position for the exerciser.

32. The exercise machine of claim 19, wherein the plurality of lights illuminate based on the position of the carriage.

33. The exercise machine of claim 19, wherein the plurality of lights are illuminated in sequence corresponding to the position of the carriage.

34. The exercise machine of claim 19, wherein the plurality of lights are non-energized at the start of an exercise.

35. The exercise machine of claim 19, wherein the plurality of lights blink at a slow rate at the start of an exercise.

36. The exercise machine of claim 19, wherein the plurality of lights blink at a frequency that increases as the carriage moves away from a first end of the rail.

37. The exercise machine of claim 19, wherein the plurality of lights are all illuminated without blinking when a proper range of motion has been reached on the carriage by the exerciser.

38. The exercise machine of claim 1, further comprising a first stationary platform connected near a first end of the rail and a second stationary platform connected near a second end of the rail.

39. The exercise machine of claim 1, further comprising an additional rail, wherein the additional rail is parallel to the rail and wherein the carriage is movably positioned upon the rail and the additional rail in a reciprocating manner between the first position and the second position.

40. The exercise machine of claim 1, wherein the carriage is comprised of a slidable seat.

41. The exercise machine of claim 1, further comprising:
a resistance flywheel connected to the rail and positioned near an end of the rail;
an elongated object connected to the resistance flywheel, wherein the elongated object is adapted to move in a reciprocating manner with respect to the resistance flywheel; and
a handle attached to the elongated object, wherein the handle is adapted for the exerciser to grasp;
wherein the carriage is comprised of a seat, wherein the carriage is adapted for the exerciser to sit upon.

42. The exercise machine of claim 41, further comprising a second sensor that continuously detects a position of the handle, wherein the second sensor transmits a position data to the processor in real-time corresponding to the position of the handle, and wherein the processor is adapted to calculate a state of the handle based on the position data received from the second sensor in real-time.

43. An exercise machine, comprising:
a rail;
a carriage movably positioned upon the rail, wherein the carriage is adapted to move in a reciprocating manner upon the rail;
a first sensor that continuously detects a position of the carriage between a first position and a second position, wherein the first sensor transmits a position data in real-time corresponding to the position of the carriage on the rail;
a processor in communication with the first sensor to receive the position data from the first sensor related to a position of the carriage, wherein the processor is adapted to calculate a state of the carriage based on the position data received in real-time; and
a means for providing real-time instruction to an exerciser when using the exercise machine on how to adjust their workout, wherein the means for providing real-time instruction is in communication with and controlled by the processor.

44. The exercise machine of claim 43, further comprising:
a resistance flywheel connected to the rail and positioned near an end of the rail;
an elongated object connected to the resistance flywheel, wherein the elongated object is adapted to move in a reciprocating manner with respect to the resistance flywheel; and
a handle attached to the elongated object, wherein the handle is adapted for the exerciser to grasp;
wherein the carriage is comprised of a seat, wherein the carriage is adapted for the exerciser to sit upon.

45. The exercise machine of claim 44, further comprising a second sensor that continuously detects a position of the handle, wherein the second sensor transmits a position data to the processor in real-time corresponding to the position of the handle, and wherein the processor is adapted to calculate a state of the handle based on the position data received from the second sensor in real-time.

46. An exercise machine monitoring and instruction system, comprising:
an exercise machine having a movable element that moves in a reciprocating manner;
a sensor that continuously detects a position of the movable element between a first position and a second position, wherein the sensor transmits a position data in real-time corresponding to the position of the movable element;
a processor in communication with the sensor to receive the position data from the sensor related to a position of the movable element, wherein the processor is adapted to calculate a state of the movable element based on the position data received in real-time; and
a means for providing real-time instruction to an exerciser when using the exercise machine on how to adjust their workout, wherein the means for providing real-time instruction is in communication with and controlled by the processor.

\* \* \* \* \*